(12) United States Patent
Kim et al.

(10) Patent No.: US 10,889,602 B2
(45) Date of Patent: Jan. 12, 2021

(54) ORGANIC COMPOUND, AND ORGANIC LIGHT EMITTING DIODE AND ORGANIC LIGHT EMITTING DISPLAY DEVICE INCLUDING THE SAME

(71) Applicant: LG DISPLAY CO., LTD., Seoul (KR)

(72) Inventors: Jun-Yun Kim, Goyang-si (KR); Hyo-Jin Noh, Paju-si (KR); Dae-Wi Yoon, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 276 days.

(21) Appl. No.: 15/842,602

(22) Filed: Dec. 14, 2017

(65) Prior Publication Data

US 2018/0186819 A1     Jul. 5, 2018

(30) Foreign Application Priority Data

Dec. 29, 2016    (KR) .......................... 10-2016-0181997

(51) Int. Cl.
     *H01L 51/50*      (2006.01)
     *C07F 7/10*       (2006.01)
     (Continued)

(52) U.S. Cl.
     CPC .............. *C07F 7/10* (2013.01); *C07D 401/10* (2013.01); *C07D 491/107* (2013.01);
     (Continued)

(58) Field of Classification Search
     None
     See application file for complete search history.

(56) References Cited

U.S. PATENT DOCUMENTS

2004/0170863 A1*   9/2004   Kim ........................ C07C 13/72
                                                         428/690
2017/0320855 A1*   11/2017   Wong ................... C07D 221/06

FOREIGN PATENT DOCUMENTS

CN          1338499 A      3/2002
CN       103946215 A      7/2014
(Continued)

OTHER PUBLICATIONS

Uoyama et al., "Highly Efficient Organic Light-Emitting Diodes from Delayed Fluorescence", Nature, vol. 492 (2012) pp. 234-240.
(Continued)

*Primary Examiner* — Gregory D Clark
(74) *Attorney, Agent, or Firm* — Birch, Stewart, Kolasch & Birch, LLP

(57) ABSTRACT

Embodiments relate to an organic compound of Formula 1:

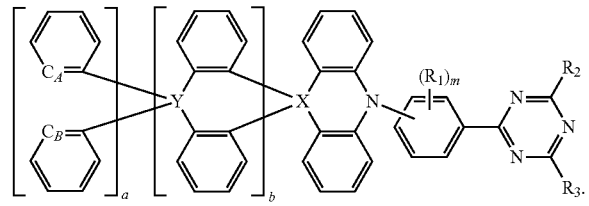

The excitons in the triplet state are engaged in emission such that the emitting efficiency of the organic compound is increased. Embodiments also relate to an organic light emitting display device with an organic light emitting diode that includes the organic compound.

9 Claims, 8 Drawing Sheets

(51) Int. Cl.
*C07D 401/10* (2006.01)
*C07D 491/107* (2006.01)
*C09K 11/06* (2006.01)
*H01L 51/00* (2006.01)
*C07F 7/08* (2006.01)

(52) U.S. Cl.
CPC ............ *C07F 7/0816* (2013.01); *C09K 11/06* (2013.01); *H01L 51/0067* (2013.01); *H01L 51/0072* (2013.01); *H01L 51/0073* (2013.01); *H01L 51/0094* (2013.01); *C09K 2211/104* (2013.01); *C09K 2211/1033* (2013.01); *C09K 2211/1059* (2013.01); *C09K 2211/1096* (2013.01); *H01L 51/5012* (2013.01); *H01L 51/5016* (2013.01); *H01L 2251/552* (2013.01)

(56) References Cited

FOREIGN PATENT DOCUMENTS

| | | | | |
|---|---|---|---|---|
| KR | 2015-173745 | * | 12/2015 | ............ C09K 11/06 |
| KR | 10-2016-0073914 A | | 6/2016 | |
| WO | WO 2016/181846 A1 | | 11/2016 | |

OTHER PUBLICATIONS

Chinese Office Action for Appl. No. 201711328118.7 dated May 19, 2020 w/ English translation.

Lin, T.A., et al, "Sky-Blue Organic Light Emitting Diode with 37% External Quantum Efficiency Using Thermally Activated Delayed Fluorescence from Spiroacridine-Triazine Hybrid." Jun. 6, 2016. Adv. Mater., vol. 26, pp. 6976-6983.

Sun, J.W., et al, "Thermally Activated Delayed Fluorescene from Azasiline Based Intramolecular Charge-Transfer Emitter (DTPDDA) and a Highly Efficient Blue Light Emitting Diode," Sep. 14, 2015, Chem. Mater., vol. 27, pp. 6675-6681.

* cited by examiner

ORGANIC COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATIONS

This application claims priority benefit of Korean Patent Application No. 10-2016-0181997 filed in the Republic of Korea on Dec. 29, 2016, which is hereby incorporated by reference into the present application.

BACKGROUND OF THE INVENTION

Field of the Invention

Embodiments of the invention relate to an organic compound, and more particularly, to an organic compound for an organic layer of an organic light emitting diode, and an organic light emitting diode and an organic light emitting display device including the organic compound.

Discussion of the Related Art

The requirements of large-size display devices have led to developments in flat panel display devices as an image displaying device. Among the flat panel display devices, an organic light emitting display (OLED) device, which may be referred to as an organic electroluminescent device or an organic light emitting diode device, has rapidly developed.

An organic light emitting diode in the OLED device is formed of a thin organic layer, which has a thickness below 2000 Å, and an image may be displayed at one side or both sides. A flexible substrate, for example, a plastic substrate, can be used as a base substrate, where elements are formed, such that a flexible or foldable display can be provided. The OLED device can be operated at a voltage lower than a voltage required to operate other display devices. Moreover, the OLED device has excellent color purity.

The OLED device includes a hole injection electrode (an anode), an electron injection electrode (a cathode) and an organic emitting layer therebetween. To increase the emitting efficiency, the organic emitting layer may include a hole injection layer (HIL), a hole transporting layer (HTL), an emitting material layer (EML), an electron transporting layer (ETL) and an electron injection layer (EIL) sequentially stacked on the hole injection electrode. In the OLED device, when the hole from an anode and the electron from the cathode are combined in the EML to generated excitons, and the excitons are transited from an excited state to a ground state such that light is emitted.

The external quantum efficiency of the emitting material for the EML can be expressed by:

$$\eta_{ext} = \eta_{S/T} \times \Gamma \times \Phi \times \eta_{out\text{-}coupling}$$

In the above equation, "$\eta_{S/T}$" is an exciton generation ratio (singlet/triplet ratio), "$\Gamma$" is the charge balance factor, "$\Phi$" is the radiative quantum efficiency, and "$\eta_{out\text{-}coupling}$" is the out-coupling efficiency.

The exciton generation ratio is a ratio of the excitons engaged in the emission. In the fluorescent material, the exciton generation ratio has a maximum value of 0.25. When the hole and the electron are combined to generate the exciton, a ratio of singlet excitons, which has a paired spin state, to triplet excitons, which has a unpaired spin state, is 1:3 according to the spin structure. In the fluorescent material, only the singlet excitons, excluding the triplet excitons of 75%, are engaged in the emission.

The charge balance factor "$\Gamma$" means a balance between the hole and the electron when generating the exciton. Generally, assuming 1:1 matching of the hole and the electrode, the charge balance factor has a value of "1". The radiative quantum efficiency "$\Phi$" is a value regarding an effective emitting efficiency of the emitting material. In the host-dopant system, the radiative quantum efficiency depends on a photoluminescence (PL) of the dopant.

The out-coupling efficiency "$\eta_{out\text{-}coupling}$" is a ratio of the light emitted from the display device to the light emitted from the emitting material. When the isotropic emitting materials are deposited in a thermal evaporation method to form a thin film, the emitting materials are randomly oriented. In this instance, the out-coupling efficiency of the display device may be assumed to be 0.2.

Accordingly, the maximum emitting efficiency of the OLED, including the fluorescent material as the emitting material, is less than approximately 5%.

To overcome the disadvantage of the emitting efficiency of the fluorescent compound, the phosphorescent compound, in which both singlet excitons and triplet excitons are engaged in emission, has been developed for the OLED.

However, the metal complex generally used as the phosphorescent compound is very expensive and has a relatively low lifetime. In addition, there is no blue phosphorescent compound meeting the requirements in emitting efficiency and reliability.

Accordingly, the development of new emitting material having excellent properties in the reliability, the emitting efficiency and the lifetime is required.

SUMMARY OF THE INVENTION

Accordingly, an embodiment of the invention is directed to an organic compound, an organic light emitting diode and an OLED device including the organic compound that substantially obviate one or more of the problems due to limitations and disadvantages of the related art.

An objective of the embodiment of the invention is to provide an organic compound having high emitting efficiency and high color purity.

Another objective of the embodiment of the invention is to provide an organic light emitting diode and an OLED device having advantages in an emitting efficiency, a color purity and a lifetime.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the embodiments of the invention, as embodied and broadly described herein, an aspect of an embodiment of the invention provides a organic compound of Formula 1. Formula 1 is given by:

[Formula 1]

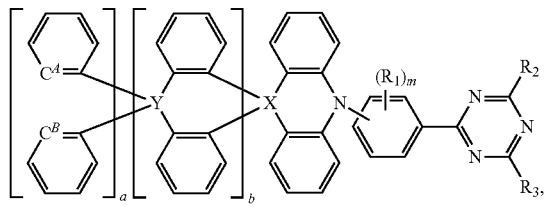

wherein each of $R_1$ to $R_3$ is independently selected from the group consisting of hydrogen, deuterium, tritium, substituted or non-substituted $C_1$ to $C_{20}$ alkyl group, substituted or non-substituted $C_1$ to $C_{20}$ alkoxy group, substituted or non-substituted $C_3$ to $C_{30}$ cycloalkyl group, substituted or non-substituted $C_3$ to $C_{30}$ hetero-cycloalkyl group, substituted or non-substituted $C_5$ to $C_{30}$ aryl group and substituted or non-substituted $C_4$ to $C_{30}$ heteroaryl group, and each of "a" and "b" is an integer of 0 to 2, and preferably 0 or 1, wherein at least one of "a" and "b" is a positive integer, and "m" is an integer of 1 to 4, wherein each of X and Y is independently carbon or silicon, and each of $C_A$ and $C_B$ is carbon, and wherein each of $C_A$ and $C_B$ has a substituent selected from the group consisting of hydrogen, deuterium, tritium, substituted or non-substituted $C_1$ to $C_{20}$ alkyl group and substituted or non-substituted $C_1$ to $C_{20}$ alkoxy group, or $C_A$ and $C_B$ are directly bonded or indirectly bonded via oxygen (O), sulfur (S) or selenium (Se).

In another aspect of the embodiment of the invention provided is an organic light emitting diode including a first electrode, a second electrode facing the first electrode, and an organic emitting layer between the first and second electrodes, the organic emitting layer including the above organic compound.

In another aspect of the embodiment of the invention provided is an organic light emitting display device including a substrate; and the above organic light emitting diode on the substrate.

It is to be understood that both the foregoing general description and the following detailed description are by example and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE EMBODIMENTS

Figure 1:
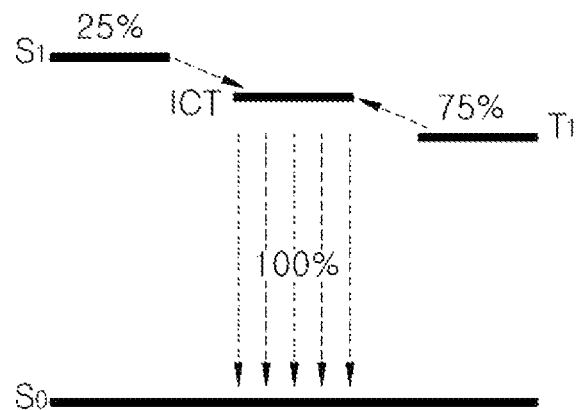
FIG. 1 is a view illustrating an emission mechanism of an organic compound according to the present disclosure.

Reference will now be made in detail to example embodiments, examples of which are illustrated in the accompanying drawings.

An organic compound in an embodiment of the present invention includes a triazine moiety as an electron acceptor moiety and an acridine moiety or a sila-acridine moiety (hereinafter (sila)acridine, which is connected to the triazine moiety via a linker, as an electron donor moiety. The organic compound has Formula 1.

[Formula 1]

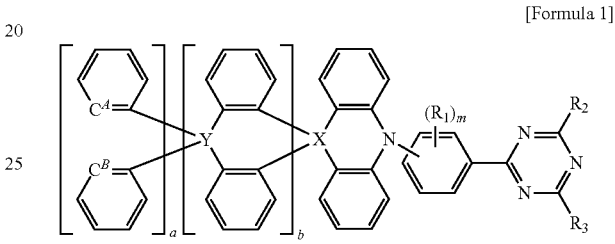

In Formula 1, each of $R_1$ to $R_3$ is independently selected from the group consisting of hydrogen, deuterium, tritium, substituted or non-substituted $C_1$ to $C_{20}$ alkyl group, substituted or non-substituted $C_1$ to $C_{20}$ alkoxy group, substituted or non-substituted $C_3$ to $C_{30}$ cycloalkyl group, substituted or non-substituted $C_3$ to $C_{30}$ hetero-cycloalkyl group, substituted or non-substituted $C_5$ to $C_{30}$ aryl group and substituted or non-substituted $C_4$ to $C_{30}$ heteroaryl group. Each of "a" and "b" is an integer of 0 to 2, and preferably 0 or 1. At least one of "a" and "b" is a positive integer (not 0). "m" is an integer of 1 to 4. Each of X and Y is independently carbon or silicon. Each of $C_A$ and $C_B$ is carbon. Each of $C_A$ and $C_B$ has a substituent selected from the group consisting of hydrogen, deuterium, tritium, substituted or non-substituted $C_1$ to $C_{20}$ alkyl group and substituted or non-substituted $C_1$ to $C_{20}$ alkoxy group, or $C_A$ and $C_B$ are directly bonded (or combined) or indirectly bonded via oxygen (O), sulfur (S) or selenium (Se).

In the term of "substituted", the substituent may include halogen-substituted or non-substituted alkyl group, halogen-substituted or non-substituted alkoxy group, halogen, cyano group, carboxyl group, carbonyl group, amino group, alkylamino group, nitro group, hydrozyl group, sulfonate group, alkyl silyl group, alkoxy silyl group, cycloakyl silyl group, aryl silyl group, substituted or non-substituted aryl group or heteroaryl group, but it is not limited thereto.

The term of "hetero", which is used in heteroaryl, heteroarylene, and so on, means that at least one carbon atom in the aromatic ring or alicyclic ring is substituted by a heteroatom being selected from the group consisting of nitrogen atom (N), oxygen atom (O) and sulfur atom (S).

In Formula 1, when each of $R_1$ to $R_3$ is alkyl group, each of $R_1$ to $R_3$ may be $C_1$ to $C_{20}$ alkyl group, and preferably $C_1$ to $C_{10}$ alkyl. When each of $R_1$ to $R_3$ is aromatic group, each of $R_1$ to $R_3$ may be selected from the group consisting of phenyl, biphenyl, terphenyl, naphthyl, anthracenyl, indenyl, indenoindenyl, biphenylenyl, indacenyl, phnalenyl, phenanthrenyl, benzophenanthrenyl, dibenzophenanthrenyl, azulenyl, pyrenyl, fluoranthenyl, chrysenyl, tetraphenyl, tetracenyl, fluorenyl, indeno-fluorenyl, spiro-fluorenyl, pyrrolyl, pyridyl (or pyridinyl), pyrimidyl (pyrimidinyl), pyrazinyl, pyridazinyl, triazinyl, tetrazinyl, imidazolyl, pyrazolyl, indolyl, isoindolyl, indazolyl, indolizinyl, pyrrolizinyl, carbazolyl, benzocarbazolyl, dibenzocarbazolyl, indolocarbazolyl, indenocarbazolyl, benzofurocarbazolyl, benzothienocarbazolyl, quinolinyl, iso-quinolinyl, phthalazinyl, quinoxalinyl, cinnolinyl, quinazolinyl, quinolizinyl, furinyl, benzoquinoxalinyl, benzo-iso-quinoxalinyl, benzoquinazolinyl, acridinyl, phenanthrolinyl, phenanthridinyl, pteridinyl, furanyl, pyranyl, oxazinyl, oxazolyl, oxadiazolyl, triazolyl, dioxynyl, benzofuranyl, dibenzofuranyl, thiopyranyl, xanthenyl, chromenyl, isochromenyl, thioazinyl, thiophenyl, benzothiophenyl, dibenzothiophenyl, difuropyrazinyl, benzofuro-dibenzofuranyl, benzothieno-benzothiophenyl, benzothieno-dibenzothiophenyl, benzothieno-benzofuranyl, benzothieno-dibenzofuranyl and N-substituted spiro-fluorenyl.

The organic compound includes the triazine moiety as an electron acceptor moiety and a (sila)acridine moiety, which is connected to the triazine moiety via a linker, as an electron donor moiety. In addition, the (sila)acridine moiety may include a spiro-aromatic moiety.

Since the (sila)acridine moiety includes three-fused six-atom rings, and the triazine moiety has big steric hindrance, a dihedral angle between the (sila)acridine moiety and the triazine moiety is increased. As a result, the conjugation between the (sila)acridine moiety and the triazine moiety is limited, the highest occupied molecular orbital (HOMO) energy state and the low unoccupied molecular orbital (LUMO) energy state are easily separated. As a result, the emitting efficiency of the organic compound is improved.

In addition, the dipole is generated in the (sila)acridine moiety to the triazine moiety such that the dipole moment in the molecule is increased and the emitting efficiency is further improved. Moreover, the (sila)acridine moiety and the triazine moiety are combined or linked in the molecule such that an overlap between the HOMO and the LUMO is reduced. As a result, a delayed fluorescence complex is generated, and the emitting efficiency is further improved.

Since a gap or a distance between the (sila)acridine moiety as an electron donor moiety and the triazine moiety as an electron acceptor moiety is increased due to the phenylene linker, an overlap between the HOMO and the LUMO is further reduced such that a gap ($\Delta E_{ST}$) between the triple energy and the singlet energy is reduced. In addition, due to the steric hindrance of the linker, the red shift problem in the light emitted from the emitting layer including the organic compound is decreased or minimized.

When a spiro-aromatic ring moiety is connected to the (sila)acridine moiety, the 3D conformation of the molecule is limited. As a result, when the organic compound emits the light, the energy loss by the 3D conformation change is not generated, and the emission spectrum is limited to a predetermined range. Accordingly, the organic compound has high color purity.

The organic compound of the present invention is used for a dopant in an organic emitting layer of an organic light emitting diode and provides a delayed fluorescent emission.

FIG. 1 is a view illustrating an emission mechanism of an organic compound according to the present disclosure.

The delayed fluorescence may be classified into a thermally activated delayed fluorescence (TADF) and a field activated delayed fluorescence (FADF). In the delayed fluorescent compound, the triplet exciton is activated by a heat or an electric field such that the hyper-fluorescence is provided beyond the maximum emitting efficiency of the related art fluorescent compound.

Namely, the triplet exciton of the delayed fluorescent compound is activated by a heat or an electric field, which is generated in or applied to a display device, such that the triplet exciton as well as the singlet exciton are engaged in the emission. Since the delayed fluorescent compound includes both the electron donor moiety and the electron acceptor moiety, an intramolecular charge transfer (ICT) may be generated. When the delayed fluorescent compound, where the ICT is generated, is used as a dopant in an EML, the singlet state "$S_1$" and the triplet state "$T_1$" are transferred into an ICT state and transited into a ground state. ($S_1 \rightarrow ICT \leftarrow T_1$) In the delayed fluorescent compound, the singlet exciton and the triplet exciton are engaged in the emission such that the internal quantum efficiency and the emitting efficiency are improved.

In the related art fluorescent compound, since the HOMO and the LUMO are dispersed throughout an entirety of the molecule, the interconversion of the HOMO and the LUMO is impossible. (Selection Rule) However, in the delayed fluorescent compound, since the overlap between the HOMO and the LUMO in the molecule is relatively small, the interaction between the HOMO and the LUMO is small. Accordingly, changes of the spin state of one electron do not affect other electrons, and a new charge transfer band, which does not comply with the Selection Rule, is generated.

In the delayed fluorescent compound, since the electron donor moiety and the electron acceptor moiety are spatially spaced apart from each other in the molecule, the dipole moment is generated in a polarized state. In the polarized state dipole moment, the interaction between the HOMO and the LUMO is further reduced such that the transition from the triplet state and the singlet state into the ICT state can be generated. As a result, not only the singlet exciton but also the triplet exciton are engaged in the emission.

When the organic light emitting diode is driven, the intersystem transition from 25% singlet state "$S_1$" excitons and 75% triplet state "$T_1$" excitons to the ICT state is generated, and the singlet and triplet excitons in the ICT are transited into the ground state "$S_0$" to emit light. As a result, the delayed fluorescent compound has a theoretic quantum efficiency of 100%.

The dopant for providing the delayed fluorescence is required to include the electron donor moiety and the electron acceptor moiety in the single molecule and have the ICT state. With a specific condition, in the ICT complex, one electron in the electron donor moiety is transferred into the electron acceptor moiety such that the charge separation in the molecule is generated. In addition, for energy transition from both the singlet state and the triplet state, the dopant for providing the delayed fluorescence is required to have an energy relation between the singlet energy level "$S_1$" and the triplet energy level "$T_1$". Namely, in the delayed fluorescent compound, a difference between the single energy level "$S_1$" and the triplet energy level "$T_1$" may be less than 0.3 eV, and preferably 0.05 eV to 0.3 eV.

The ICT complex having the delayed fluorescent property is formed by an outer stimulations. It can be verified by comparing the absorption peak and the emission peak of the solution of the compounds.

$$\Delta v = v_{abs} - v_{fl} \frac{2\Delta \mu^2}{hca^3} \Delta f + \text{constant (Lipper Matage equation)}$$

In the above equation, "Δυ" is the Stock-shift value, and "$υ_{abs}$" and "$υ_{fl}$" are the wave-number of the maximum absorption peak and the maximum emission peak, respectively. "h" is Planck's constant, "c" is the velocity of light, "a" is the onsager cavity radius, and "Δμ" is a difference between the dipole moment of the excited state and the dipole moment of the ground state. ($Δμ=μ_e-μ_g$)

"Δf" is a value indicating the orientational polarizability of the solvent and may be a function of the dielectric constant of the solvent (ε) and the refractive index of the solvent (n).

$$\Delta f = \frac{\varepsilon - 1}{2\varepsilon + 1} - \frac{n^2 - 1}{2n^2 + 1}$$

Since the intensity of dipole moment in the excited state is determined by the peripheral polarity (e.g., the polarity of the solvent), the ICT complex can be verified by comparing the absorption peak and the emission peak of the solution of the compounds.

The orientational polarizability (Δf) of the mixed solvent can be calculated by using the orientational polarizability of each pure solvent and their mole fraction. When "Δf" and "Δυ" are linearly plotted by using above "Lippert-Mataga equation", the compound may provide the ICT emission. Namely, when the ICT complex is stabilized according to the orientational polarizability of the solvent, the emission peak is shifted in a long wavelength according to the degree of the stabilization. Accordingly, when the compound provides the ICT emission, "Δf" and "Δυ" are plotted in a linear line. When "Δf" and "Δυ" are plotted in a linear line, the compound provides the ICT emission.

In the organic compound of the above Formula 1, the (sila)acridine moiety as the electron donor and the triazine moiety as the electron acceptor exist in a single molecule, the organic compound has the delayed fluorescent property. Since the steric hindrance between the (sila)acridine moiety and the triazine moiety is relatively big, the conjugation structure (configuration) is limited and the energy in the organic compound is easily separated into the HOMO energy state and the LUMO energy state. In addition, the dipole is generated in the (sila)acridine moiety to the triazine moiety such that the dipole moment in the molecule is increased and the emitting efficiency is improved. Moreover, the (sila)acridine moiety and the triazine moiety are combined or linked in the molecule such that an overlap between the HOMO and the LUMO is reduced. Further, since the (sila)acridine moiety and the triazine moiety are connected to each other via the phenylene linker, the overlap between the HOMO and the LUMO is further reduced such that the difference between the triplet energy level and the singlet energy level ($\Delta_{EST}$) is also reduced. When the spiro-aromatic ring moiety may be connected to the (sila)acridine moiety, the 3D conformation of the molecule is limited such that there is no energy loss in the emission and high purity blue emission is provided.

The organic compound in the above Formula 1 may be represented by Formula 2 or Formula 3.

[Formula 2]

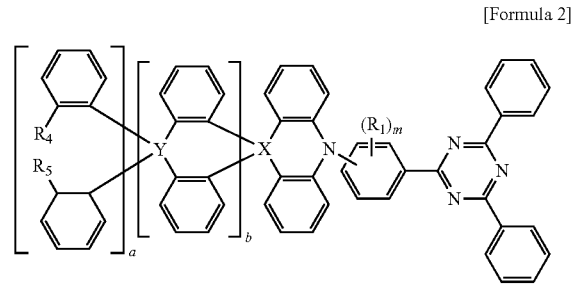

[Formula 3]

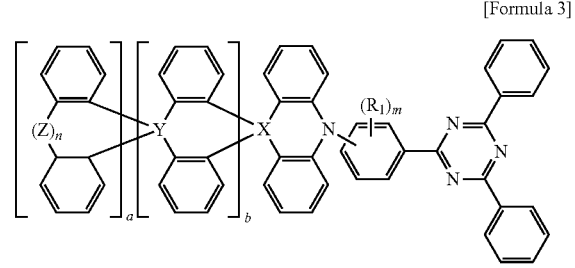

In Formulas 2 and 3, $R_1$, a, b, m, X and Y are same as defined in Formula 1. In Formula 2, each of $R_4$ and $R_5$ is independently selected from hydrogen, deuterium, tritium and $C_1$ to $C_{20}$ alkyl group. In Formula 3, Z is oxygen, sulfur or selenium, and n is 0 or 1.

For example, the organic compound of the present invention is one of materials represented by Formula 4.

[Formula 4]

compound 1

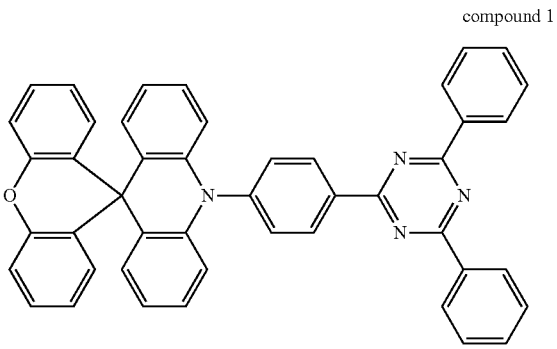

compound 2

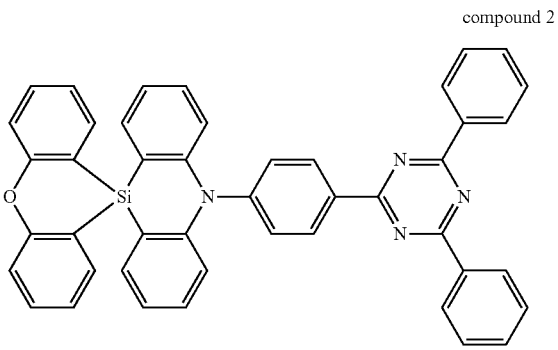

compound 3
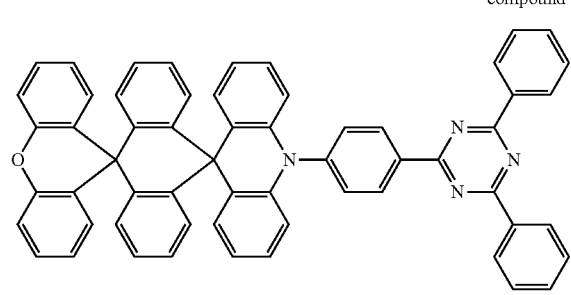
compound 4
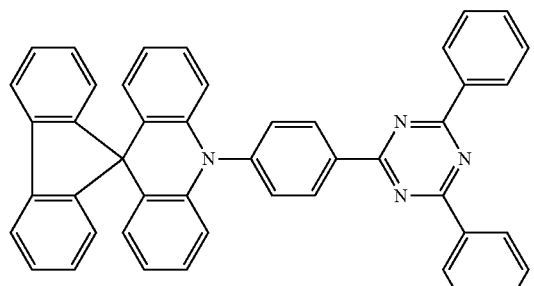
compound 5
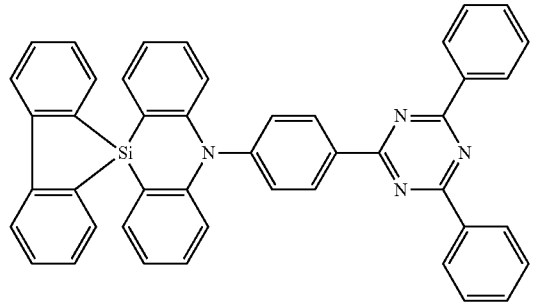
compound 6
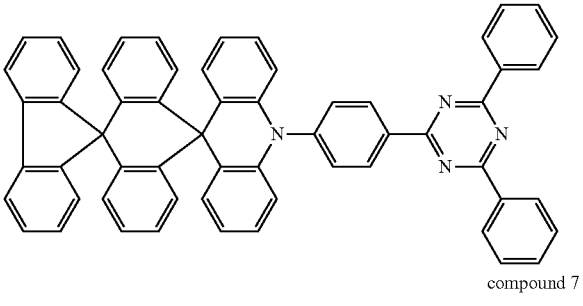
compound 7
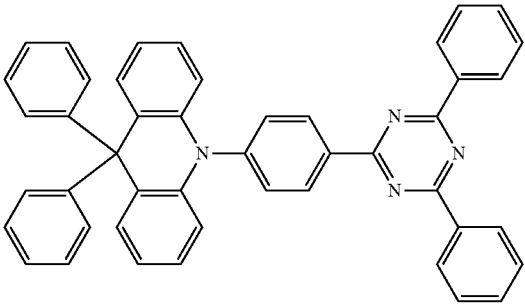
compound 8
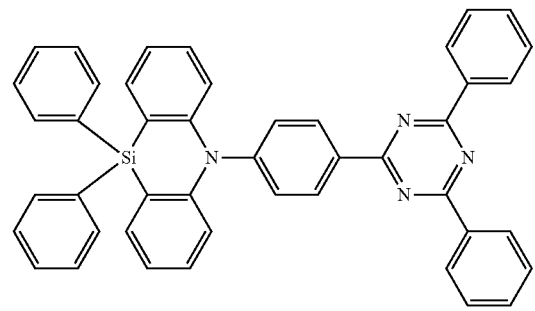
compound 9
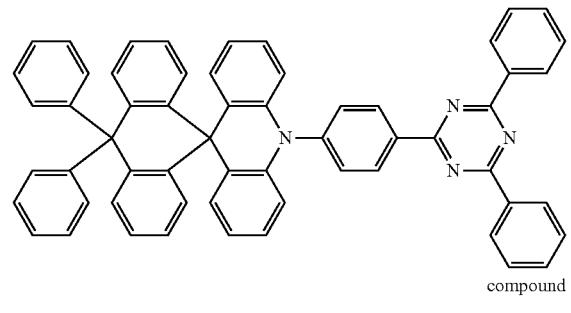
compound 10
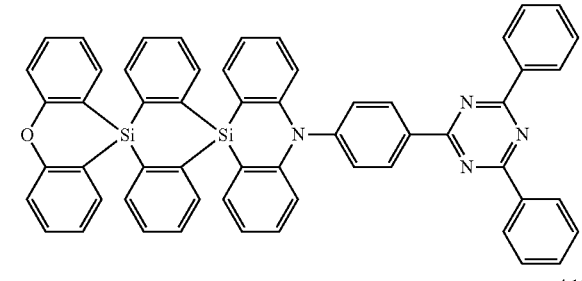
compound 11
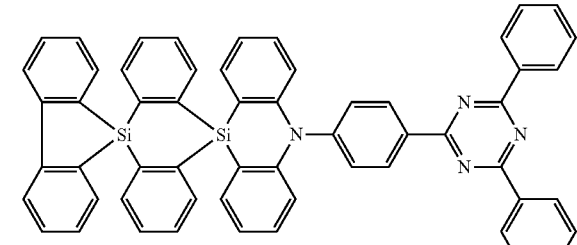
compound 12
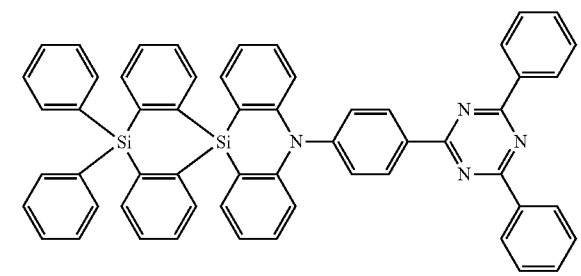
As mentioned above, in the organic compound of Formulas 2 to 4, the triazine moiety as the electron acceptor is connected to the (sila)acridine moiety as the electron donor via the linker, and the spiro-aromatic moiety is connected to the (sila)acridine moiety.

Since the (sila)acridine moiety as the electron donor and the triazine moiety as the electron acceptor exist in a single molecule, the dipole moment in the organic compound is increased and the HOMO energy level and the LUMO energy level are easily separated. In addition, the organic compound has a molecular structure, in which the dipole moment is increased. As a result, the organic compound has the delayed fluorescent property.

When the spiro-aromatic ring moiety is connected to the (sila)acridine moiety, the 3D conformation of the molecule is limited. As a result, when the organic compound is used as a dopant in the organic light emitting diode, the organic light emitting diode having improved emitting efficiency and color purity is provided.

Figure 2:
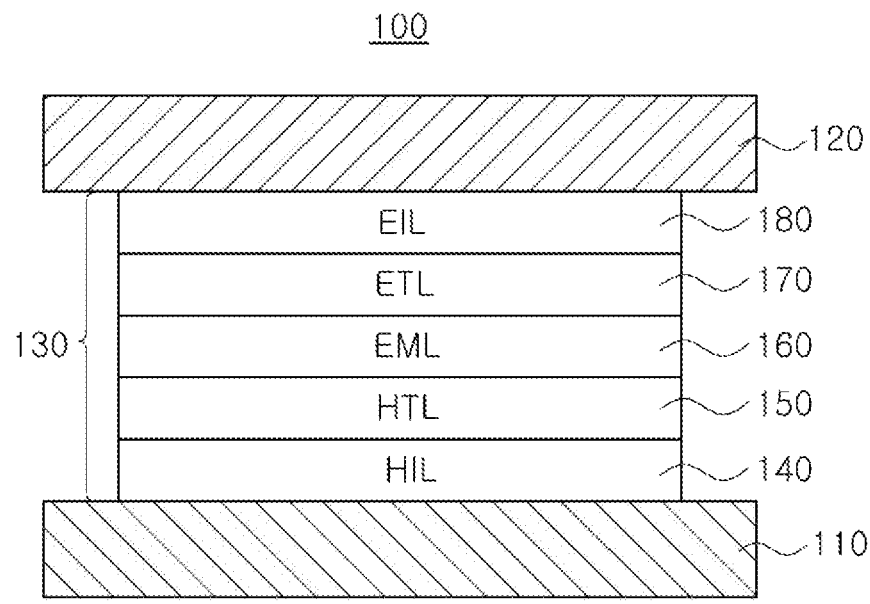
FIG. 2 is a schematic cross-sectional view of an organic light emitting diode according to a first embodiment of the present invention.

FIG. 2 is a schematic cross-sectional view of an organic light emitting diode according to a first embodiment of the present invention.

As shown in FIG. 2, the organic light emitting diode 100 is provided on a substrate (not shown). The organic light emitting diode 100 includes a first electrode 110, a second electrode 120 and an organic emitting layer 130 therebetween. For example, the organic emitting layer 130 may include a hole injection layer (HIL) 140, a hole transfer layer (HTL) 150, an emitting material layer (EML) 160, an electron transfer layer (ETL) 170 and an electron injection layer (EIL) 180 sequentially stacked on the first electrode 110.

The first electrode 110 may serve as an anode providing a hole into the EML 160. The first electrode 110 is formed of a conductive material having a relatively high work function. For example, the first electrode may be formed of a transparent conductive material, e.g., indium-tin-oxide (ITO), indium-zinc-oxide (IZO), indium-tin-zinc oxide (ITZO), tin oxide (SnO), zinc oxide (ZnO), indium-copper-oxide (ICO) or Al:ZnO (AZO).

The second electrode 120 may serve as a cathode providing an electron into the EML 160. The second electrode 120 may be formed of a conductive material having a relatively low work function. For example, the second electrode 120 may be formed of Al, Mg, Ca, Ag or their alloy.

The HIL 140 is positioned between the first electrode 110 and the HTL 150. The interface property between the first electrode 110 of an inorganic material and the HTL 150 of an organic material is improved by the HIL 140. For example, the HIL 140 may be formed of a hole injection material such as 4,4',4"-tris(3-methylphenylphenylamino) triphenylamine (MTDATA), copper phthalocyanine (CuPc), Tris(4-carbazoyl-9-yl-phenyl)amine (TCTA), N,N'-diphenyl-N,N'-bis(1-naphthyl)-1,1'-biphenyl-4,4"-diamine (NPB or NPD), 1,4,5,8,9,12-hexaazatriphenyl enehexacarbonitrile (HATCN), 1,3,5-tris[4-(diphenylamino)phenyl]benzene (TDAPB), poly(3,4-ethylenedioxythiophene)polystyrene sulfonate (PEDOT/PSS) or N-(biphenyl-4-yl)-9,9-dimethyl-N-(4-(9-phenyl-9H-carbazol-3-yl)phenyl)-9H-fluoren-2-amine. The HIL 140 may be omitted.

The HTL 150 is positioned between the HIL 140 and the EML 160. For example, the HTL 150 may be formed of N,N'-diphenyl-N,N'-bis(3-methylphenyl)-1,1'-biphenyl-4,4'-diamine (TPD), NPD, 4,4'-bis(N-carbazolyl)-1,1'-biphenyl (CBP), N-(biphenyl-4-yl)-9,9-dimethyl-N-(4-(9-phenyl-9H-carbazol-3-yl)phenyl)-9H-fluoren-2-amine or N-(biphenyl-4-yl)-N-(4-(9-phenyl-9H-carbazol-3-yl)phenyl)biphenyl-4-amine, but it is not limited thereto.

The EML 160 includes a host and a dopant. For example, in the EML 160, the dopant is doped into the host by a weight % of about 1 to 50 with respect to the host, and the EML 160 emits the blue light.

The dopant may be the organic compound of one of Formulas 1 to 4. Namely, the dopant in the EML 160 has the delayed fluorescent property.

As mentioned above, the organic compound having the delayed fluorescent compound is activated by the heat or the electric field to have the intermediate energy state such as the ICT complex. In the organic compound, since the exciton having the singlet energy state and the exciton having the triplet energy state are engaged in the emission, the emitting efficiency of the organic light emitting diode 100 is improved.

The difference ($\Delta E_{ST}$) between the singlet energy ($S_1$) of the dopant and the triplet energy ($T_1$) of the dopant is less than 0.3 eV, and preferably 0.05 to 0.3 eV. When the difference between the singlet energy ($S_1$) of the dopant and the triplet energy ($T_1$) of the dopant is less than 0.3 eV, the single energy state and the triplet energy state are transited into the intermediate energy state and finally transited into the ground state. As a result, the quantum efficiency of the dopant is improved. As the difference "$\Delta E_{ST}$" is smaller, the emitting efficiency is higher. When the difference "$\Delta E_{ST}$" is less than 0.3 eV, the organic compound is activated by the heat or the electric field such that the singlet exciton and the triplet exciton is transited into the intermediate energy state such as the ICT complex.

Figure 3:
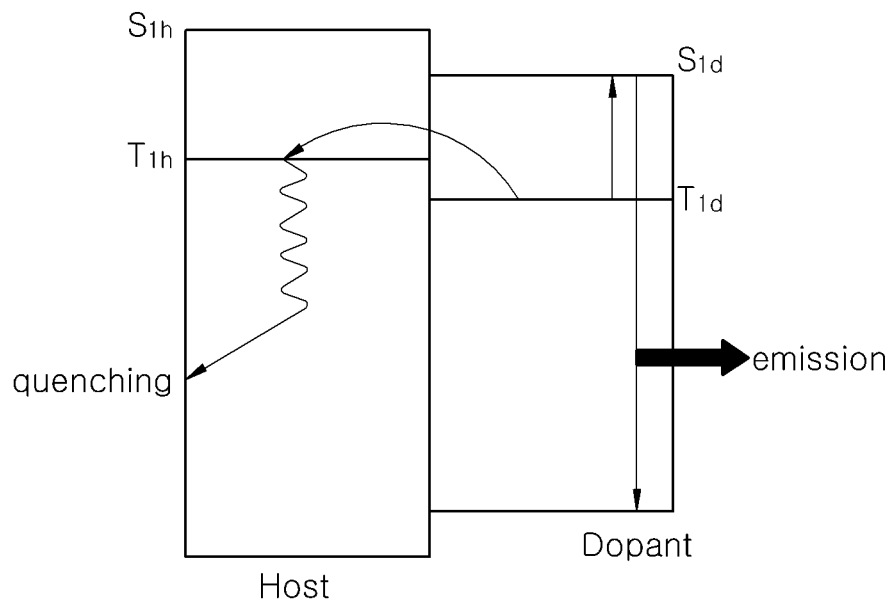
FIG. 3 is a view illustrating an energy level relation between a host and a dopant in an EML of an organic light emitting diode of the present invention.

On the other hand, to provide the delayed fluorescent property, the dopant should be induced such that the triplet energy of the dopant is not quenched. Referring to FIG. 3, which is a view illustrating an energy level relation between a host and a dopant in an EML of an organic light emitting diode of the present invention, the energy level of the host is controlled based on the energy level of the dopant.

The triplet energy level "$T_{1h}$" of the host is greater than the triple energy level "$T_{1d}$" of the dopant. When the triplet energy level "$T_{1h}$" of the host is not sufficiently greater than the triple energy level "$T_{1d}$" of the dopant, the triplet exciton of the dopant is transited into the triplet energy level "$T_{1h}$" of the host such that the quenching problem of the dopant may be generated. Namely, the triplet exciton of the dopant does not anticipate in the emission.

In addition, the HOMO level and the LUMO level of the host and the dopant are required to be controlled. For example, a difference between the HOMO of the host "$HOMO_{Host}$" and the HOMO of the dopant "$HOMO_{Dopant}$" or a difference between the LUMO of the host "$LUMO_{Host}$" and the LUMO of the dopant "$LUMO_{Dopant}$" is less than 0.5 eV ($|HOMO_{Host}-HOMO_{Dopant}|\leq 0.5$ eV or $|LUMO_{Host}-LUMO_{Dopant}|\leq 0.5$ eV), and preferably 0.1 to 0.5 eV. In this instance, the charge transfer efficiency from the host to the dopant may be improved such that the emission efficiency of the organic light emitting diode is improved.

For example, the host of the EML 160 may be selected from the group consisting of 9-(3-(9H-carbazol-9-yl)phenyl)-9H-carbazole-3-carbonitrile (mCP—CN), 3,3'-bis(N-carbazolyl)-1,1'-biphenyl (mCBP), (oxybis(2,1-phenylene)) bis(diphenylphosphine oxide (DPEPO), 9-(4-(9H-carbazol-9-yl)phenyl)-9H-3,9'-bicarbazole and 9-(3-(9H-carbazol-9-yl)phenyl)-9H-3,9'-bicarbazole, but it is not limited thereto.

Referring again to FIG. 2, the ETL 170 and the EIL 180 may be sequentially stacked between the EML 160 and the second electrode 120. The electron from the second electrode 120 is provided into the EML 160.

For example, the ETL 170 may be formed of a derivative of oxadiazole, triazole, phenanthroline, benzoxazole, benzothiazole, benzimidazole or triazine. The material of the ETL 170 may be selected from the group consisting of tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 2-[4-(9,10-di-2-naphthalenyl-2-anthracenyl)phenyl]-1-phenyl-1H-benzimidazole, Bis(2-methyl-8-quinolinolato-N1,O8)-(1,1'-biphenyl-4-olato)aluminum (BAlq), 3-(biphenyl-4-yl)-5-(4-terbutylphenyl)-4-phenyl-4H-1,2,4-triazole (TAZ), 4,7-diphenyl-1,10-phenanthroline (Bphen), tris(phenylquinoxaline) (TPQ) and 1,3,5-tris(N-phenylbenzimiazole-2-yl)benzene (TPBi), but it is not limited thereto.

The EIL 180 is positioned between the ETL 170 and the second electrode 120. The EIL 180 may include an alkali metal/alkali earth metal halide compound, e.g., LiF, CsF, NaF or $BaF_2$, or an organo-metallic compound, e.g., lithium quinolate (Liq), lithium benzoate or sodium stearate, but it is not limited thereto.

In the organic light emitting diode 100, the EML 160 includes the organic compound of the present invention, which has the delayed fluorescent property, as the dopant. Since the singlet exciton and the triplet exciton of the dopant are engaged in the emission, the emission efficiency of the organic light emitting diode 100 is improved.

As mentioned above, since the triazine moiety as the electron acceptor and the (sila)acridine moiety as the electron donor exist in the molecule, the dipole moment is increased and the separation into the HOMO level and the LUMO level is easily generated such that the organic compound has the delayed fluorescent property. In addition, the spiro-aromatic moiety is further connected to the (sila) acridine moiety, the 3D conformation is strongly limited. Accordingly, in the organic light emitting diode 100 including the organic compound of the present invention, the emission efficiency and the color purity are improved.

Figure 4:
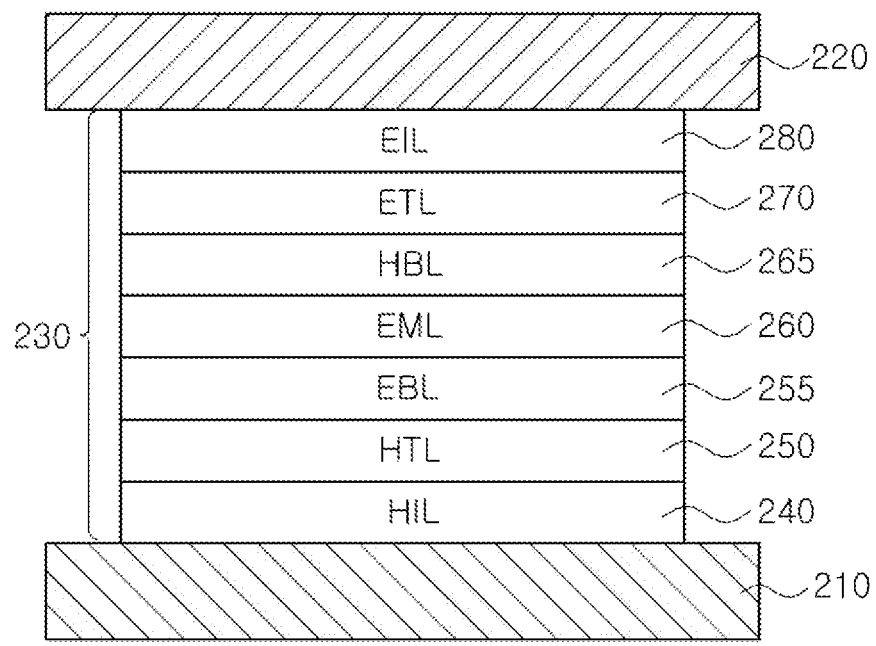
FIG. 4 is a schematic cross-sectional view of an organic light emitting diode according to a second embodiment of the present invention.

The organic light emitting diode may further includes at least one exciton blocking layer. Referring to FIG. 4, which is a schematic cross-sectional view of an organic light emitting diode according to a second embodiment of the present invention, the organic light emitting diode 200 includes the first electrode 210, the second electrode 220 and the organic emitting layer 230 therebetween. For example, the organic emitting layer 230 may include the HIL 240, the HTL 250, a first exciton blocking layer 255 as an electron blocking layer (EBL), the EML 260, a second exciton blocking layer 265 as a hole blocking layer (HBL), the ETL 270 and the EIL 280 sequentially stacked on the first electrode 210.

The first electrode 210 may serve as an anode and be formed of a relatively high work function material, e.g., ITO, IZO, ITZO, ZnO, ICO or AZO. The second electrode 220 may serve as a cathode and be formed of a relatively low work function material, e.g., Al, Mg, Ca, Ag or their ally.

The HIL 240 is positioned between the first electrode 210 and the HTL 250 and may include a material selected from the group consisting of MTDATA, CuPc, TCTA, NPB (NPD), HAT-CN, TDAPB, PEDOT/PSS and N-(biphenyl-4-yl)-9,9-dimethyl-N-(4-(9-phenyl-9H-carbazol-3-yl)phenyl)-9H-fluoren-2-amine.

The HTL 250 is positioned between the HIL 240 and the first exciton blocking layer 255. The HTL 250 may include a material selected from the group consisting of TPD, NPD, CBP, N-(biphenyl-4-yl)-9,9-dimethyl-N-(4-(9-phenyl-9H-carbazol-3-yl)phenyl)-9H-fluoren-2-amine and N-(biphenyl-4-yl)-N-(4-(9-phenyl-9H-carbazol-3-yl)phenyl)biphenyl-4-amine The EML 260 is positioned between the first and second exciton blocking layers 255 and 265. The EML 260 includes the host and the dopant having a doping ratio of about 1 to 50 weight %. For example, the dopant of the organic compound of the present invention is doped into the host, e.g., mCP—CN, mCBP or DPEPO.

The ETL 270 is positioned between the second exciton blocking layer 265 and the EIL 280. For example, the ETL 270 may include a material selected from the group consisting of $Alq_3$, PBD, spiro-PBD, Liq, 2-[4-(9,10-di-2-naphthalenyl-2-anthracenyl)phenyl]-1-phenyl-1H-benzimidazole, BAlq, TAZ, Bphen, TPQ, and TPBi.

The EIL 280 is positioned between the ETL 270 and the second electrode 220. For example, the EIL 280 may include an alkali metal/alkali earth metal halide compound, e.g., LiF, CsF, NaF or $BaF_2$, or an organo-metallic compound, e.g., lithium quinolate (Liq), lithium benzoate or sodium stearate.

When the hole is transferred toward the second electrode 220 beyond the EML 260 or the electron is transferred toward the first electrode 210 beyond the EML 260, the lifetime and the emission efficiency of the organic light emitting diode are decreased. To prevent these problems, at least one of the first and second exciton blocking layers 255 and 265, i.e., the EBL and the HBL, is formed adjacent to the EML 260.

For example, to block the electron, the first exciton blocking layer 255 is formed between the HTL 250 and the EML 260. The first exciton blocking layer 255 may be formed of a material selected from the group consisting of TCTA, tris[4-(diethylamino)phenyl]amine, N-(biphenyl-4-yl)-9,9-dimethyl-N-(4-(9-phenyl-9H-carbazol-3-yl)phenyl)-9H-fluoren-2-amine, tri-p-tolylamine, 1,1-bis(4-(N,N'-di (ptolyl)amino)phenyl)cyclohexane (TAPC), MTDATA, mCP, mCBP, CuPc, N,N'-bis[4-[bis(3-methylphenyl)amino] phenyl]-N,N'-diphenyl-[1,1'-biphenyl]-4,4'-diamine (DNTPD) and TDAPB.

In addition, to block the hole, the second exciton blocking layer 265 is formed between the EML 260 and the ETL 270. The second exciton blocking layer 265 may include a derivative of oxadiazole, triazole, phenanthroline, benzoxazole, benzothiazole, benzimidazole or triazine.

For example, the material of the second exciton blocking layer 265 has the HOMO level being lower than that of the EML 260. The material of the second exciton blocking layer 265 may be selected from the group consisting of 2,9-dimethyl-4,7-diphenyl-1,10-phenanthroline (BCP), bis-4,6-(3,5-di-3-pyridylphenyl)-2-methylpyrimidine (B3PYMPM), BAlq, $Alq_3$, PBD, spiro-PBD and Liq.

In the organic light emitting diode 200, the EML 260 includes the organic compound of the present invention, which has the delayed fluorescent property, as the dopant. Since the singlet exciton and the triplet exciton of the dopant are engaged in the emission, the emission efficiency of the organic light emitting diode 200 is improved.

As mentioned above, since the triazine moiety as the electron acceptor and the (sila)acridine moiety as the electron donor exist in the molecule, the dipole moment is increased and the separation into the HOMO level and the LUMO level is easily generated such that the organic compound has the delayed fluorescent property. In addition, the spiro-aromatic moiety is further connected to the (sila) acridine moiety, the 3D conformation is strongly limited. Accordingly, in the organic light emitting diode 200 including the organic compound of the present invention, the emission efficiency and the color purity are improved.

In addition, the organic light emitting diode 200 includes the first and second exciton blocking layers 255 and 265 such that the emission in an interface between the HTL 250 and the EML 260 and/or between the ETL 270 and the EML 260 is prevented. As a result, there are additional advantages in the lifetime and the emission efficiency in the organic light emitting diode 200.

Figure 5:
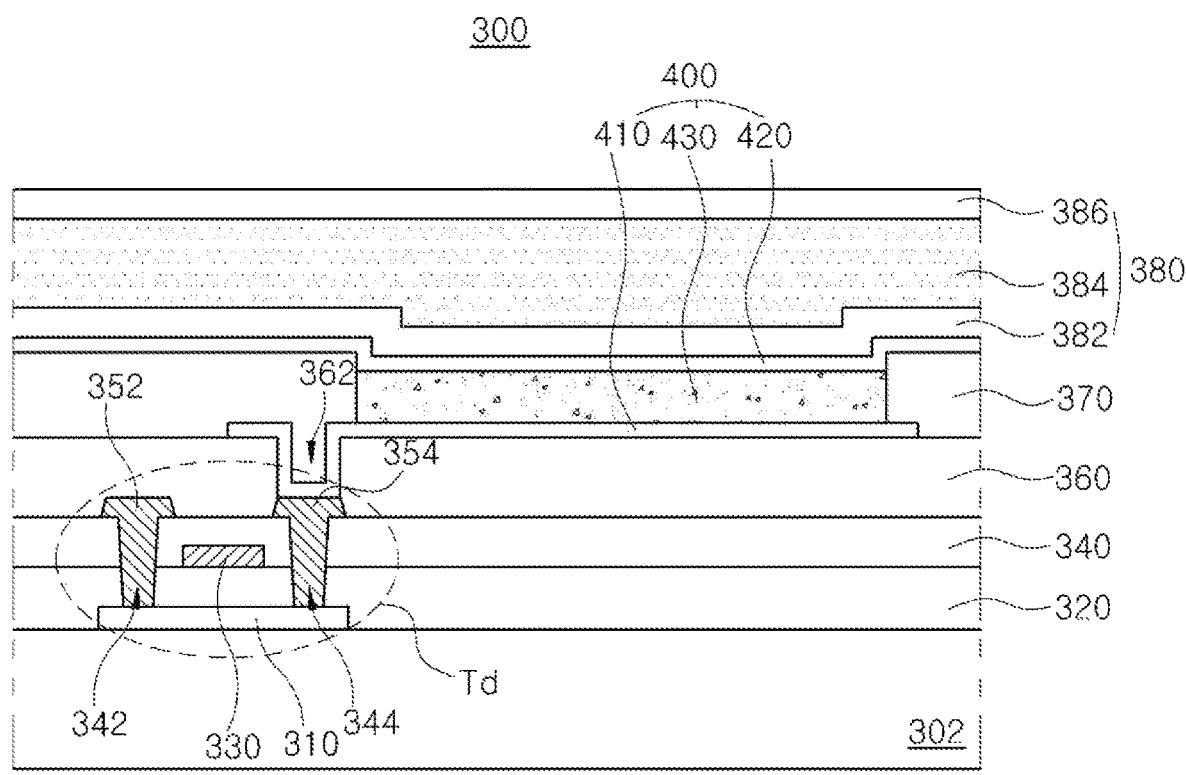
FIG. 5 is a schematic cross-sectional view of an OLED device according to the present invention.

The organic light emitting diode has various applications, e.g., an organic light emitting display (OLED) device or a lightening device. Referring to FIG. 5, which is a schematic cross-sectional view of an OLED device according to the present invention, the OLED device 300 includes a driving thin film transistor (TFT) Td, a planarization layer 360 covering the driving TFT Td, an organic light emitting diode 400 on the planarization layer 360 and connected to the driving TFT Td.

The driving TFT Td includes a semiconductor layer 310, a gate electrode 330, a source electrode 352 and a drain electrode 354. The driving TFT Td in FIG. 5 has a coplanar structure.

A substrate 302 may be a glass substrate, a thin flexible substrate or a polymer plastic substrate. For example, the substrate 302 may be formed of polyimide (PI), polyethersulfone (PES), polyethylenenaphthalate (PEN) or polyethylene terephthalate (PET). The first substrate 302, on which the driving TFT Td and the organic light emitting diode E are formed, may be referred to as an array substrate.

The semiconductor layer 310 is formed on the substrate 302. The semiconductor layer 310 may be formed of an oxide semiconductor material. When the semiconductor layer 310 includes the oxide semiconductor material, a light-shielding pattern (not shown) may be formed under the semiconductor layer 310. The light to the semiconductor layer 310 is shielded or blocked by the light-shielding pattern such that thermal degradation of the semiconductor layer 310 can be prevented. On the other hand, when the semiconductor layer 310 includes polycrystalline silicon, impurities may be doped into both sides of the semiconductor layer 310.

A gate insulating layer 320 is formed on the semiconductor layer 310 and over an entire surface of the substrate 302. The gate insulating layer 320 may be formed of an inorganic insulating material such as silicon oxide or silicon nitride.

The gate electrode 330, which is formed of a conductive material, e.g., metal, is formed on the gate insulating layer 320 to correspond to a center of the semiconductor layer 310. In addition, a gate line (not shown) and a first capacitor electrode (not shown) may be formed on the gate insulating layer 320. The gate line may extends along a first direction, and the first capacitor electrode may be connected to the gate electrode 330. The gate insulating layer 320 in FIG. 5 covers an entire surface of the substrate 302. Alternatively, the gate insulating layer 320 may be patterned to have the same shape as the gate electrode 330.

An interlayer insulating layer 340, which is formed of an insulating material, is formed on an entire surface of the substrate 302 including the gate electrode 330. The interlayer insulating layer 340 may be formed of an inorganic insulating material, e.g., silicon oxide or silicon nitride, or an organic insulating material, e.g., benzocyclobutene or photo-acryl.

The interlayer insulating layer 340 includes first and second semiconductor contact holes 342 and 344 exposing both sides of the semiconductor layer 310. The first and second semiconductor contact holes 342 and 344 are positioned at both sides of the gate electrode 330 to be spaced apart from the gate electrode 330. In FIG. 5, the first and second semiconductor contact holes 342 and 344 are formed through the gate insulating layer 320 as well as the interlayer insulating layer 340. Alternatively, when the gate insulating layer 320 has the same shape as the gate electrode 330, the first and second semiconductor contact holes 342 and 344 may be formed in the interlayer insulating layer 340 except the gate insulating layer 320.

The source electrode 352 and the drain electrode 354, which are formed of a conductive material, e.g., metal, are formed on the interlayer insulating layer 340. In addition, a data line (not shown) extending along a second direction, a power line (not shown) and a second capacitor electrode (not shown) may be formed on the interlayer insulating layer 340. The data line crosses the gate line to define a pixel region, and the power line is spaced apart from and parallel to the data line. The second capacitor electrode is connected to the drain electrode 354 and overlaps the first capacitor electrode to form a storage capacitor with the interlayer insulating layer 340.

The source electrode 352 and the drain electrode 354 are spaced apart from each other with respect to the gate electrode 330 and respectively contact both sides of the semiconductor layer 310 through the first and second semiconductor contact holes 342 and 344.

In the driving TFT Td, the gate electrode 330, the source electrode 352 and the drain electrode 354 are positioned over the semiconductor layer 310. Namely, the driving TFT Td has a coplanar structure.

Alternatively, in the driving TFT Td, the gate electrode may be positioned under the semiconductor layer, and the source and drain electrodes may be positioned over the semiconductor layer such that the driving TFT Td may have an inverted staggered structure. In this instance, the semiconductor layer may include amorphous silicon.

A switching TFT (not shown) is formed on the substrate 302. The switching TFT may have substantially the same structure as the driving TFT Td. The gate electrode 330 is connected to a drain electrode of the switching TFT, and the source electrode 352 is connected to the power line. A gate electrode and a source electrode of the switching TFT are connected to the gate line and the data line, respectively.

Although not shown, the OLED device 300 may further include a color filter pattern. For example, red, green and blue color filter patterns may be formed in each pixel region to overlap the organic emitting layer 430 of the organic light emitting diode 400.

In the OLED device 300 of a bottom-emission type, the color filter pattern may be positioned between the interlayer insulating layer 340 and the organic light emitting diode 400. Alternatively, in the OLED device 300 of a top-emission type, the color filter pattern may be positioned on or over the second electrode 420 of the organic light emitting diode 400.

A planarization layer 360, which provides a flat top surface and includes a drain contact hole 362 exposing the drain electrode 354 of the driving TFT Td, is formed to cover the driving TFT Td. The drain contact hole 362 may be spaced apart from the second semiconductor contact hole 344 in a plane.

The organic light emitting diode 400 is disposed on the planarization layer 360 and includes a first electrode 410, an organic emitting layer 430 and a second electrode 420. The first electrode 410 is connected to the drain electrode 354 of the driving TFT Td.

The first electrode 410 is separated in each pixel region. The first electrode 410 may serve as an anode and be formed of a relatively high work function material, e.g., ITO, IZO, ITZO, ZnO, ICO or AZO.

In the top-emission type OLED device 300, a reflection electrode or a reflection layer may be formed under the first electrode 410. The reflection electrode or the reflection layer may be formed of aluminum-palladium-copper (APC) alloy.

A bank 370 is formed on edges of the first electrode 410 and the planarization layer 360. The bank 370 exposes a center of the first electrode 410.

The organic emitting layer 430 is formed on the first electrode 410. The organic emitting layer 430 may have a multi-layered structure of the HIL, the HTL, the EML, the ETL and the EIL and may further include the EBL and the HBL.

The second electrode 420 is formed on an entire surface of the substrate 302 including the organic emitting layer 430. The second electrode 420 may serve as a cathode and be formed of a relatively low work function material, e.g., Al, Mg, Ca, Ag or their ally.

To prevent moisture penetration into the organic light emitting diode 400, an encapsulation film 380 may be formed on the organic light emitting diode 400. For example, the encapsulation film 380 may have a multi-layered structure of a first inorganic layer 382, an organic layer 384 and a second inorganic layer 386, but it is not limited thereto.

In the organic light emitting diode 400 of the OLED device 300, the organic emitting layer 430 includes the organic compound of the present invention, which has the delayed fluorescent property, as the dopant. Since the singlet exciton and the triplet exciton of the dopant are engaged in the emission, the emission efficiency of the OLED device 400 is improved.

As mentioned above, since the triazine moiety as the electron acceptor and the (sila)acridine moiety as the electron donor exist in the molecule, the dipole moment is increased and the separation into the HOMO level and the LUMO level is easily generated such that the organic compound has the delayed fluorescent property. In addition, the spiro-aromatic moiety is further connected to the (sila)acridine moiety, the 3D conformation is strongly limited. Accordingly, in the OLED device 300 including the organic compound of the present invention, there are advantages in the emission efficiency, the color purity and the lifetime.

Synthesis

1. Synthesis of Compound 1
(1) Compound "1a"

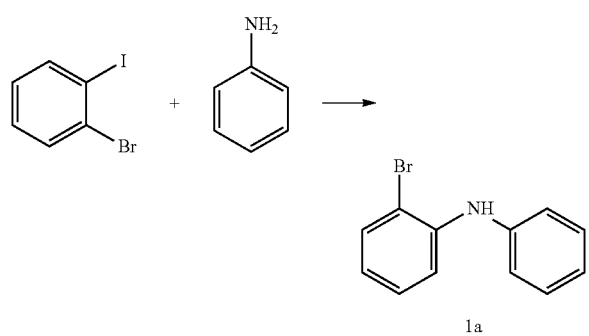

1a

In the N$_2$ gas purging system, 1-bromo-2-iodobenzene (106 mmol) and the toluene solvent were stirred. Aniline (106 mmol) was added, and the mixture was bubbled with Ar gas under the room temperature for about 30 minutes. After sodium t-butoxide (148 mmol) was added, 4,5-bis (diphenylphosphino)-9,9-dimethylxanthene (Xantphos, 2.10 mmol) and tris(dibenzylideneacetone)dipalladium(0) (Pd$_2$(dba)$_3$, 0.53 mmol) were further added. The mixture was refluxed and stirred for more than 24 hrs. After completion of the reaction, the solvent was removed, and the mixture was extracted using distilled water and ethylacetate. The moisture was removed from the extracted organic layer using magnesium sulfate, and the solvent was removed. By wet-refine process in the column chromatography using hexane and ethylacetate, the compound "1a" of light-yellow liquid was obtained. (yield: 95%)

(2) Compound "1b"

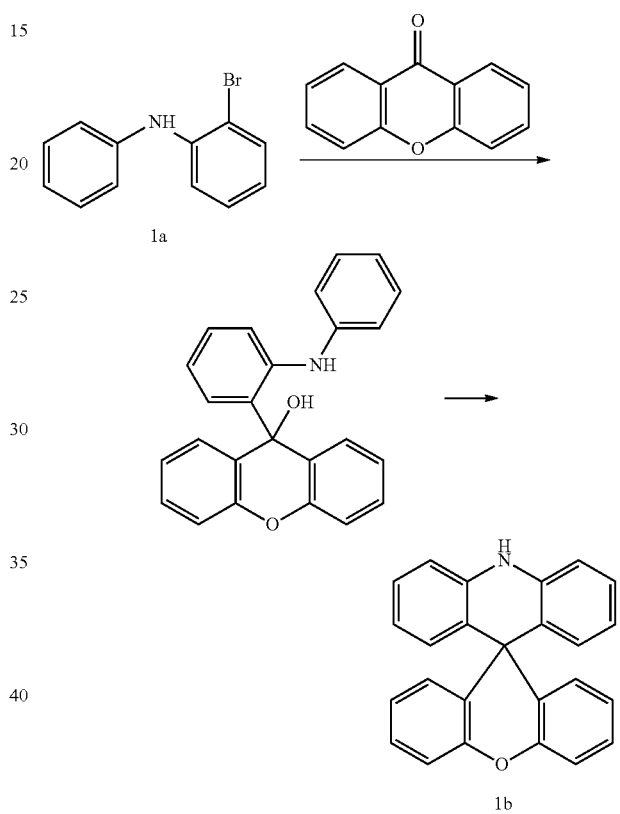

In the vacuum-dry flask under the N$_2$ gas purging system, the compound "1a" (110 mmol) and the tetrahydrofuran solvent was stirred. The mixture was additionally stirred under the temperature of −78° C. for 10 minutes, and butyl-lithium (240 mmol) was slowly dropped. After the mixture was stirred for 60 minutes, xanthone (130 mmol) was added, and the mixture was stirred for more than 24 hrs. The mixture was concentrated under the reduced pressure, the organic layer was extracted by CHCl$_3$. The moisture was removed from the extracted organic layer using magnesium sulfate, and the solvent was removed. Chloroform and methansulfonic acid (120 mmol) were added, and the mixture was refluxed and stirred for more than 24 hrs. The mixture was cooled into the room temperature, and NaHCO$_3$ aqueous solution in excess amount was slowly input and stirred. The mixture was extracted by methylenechloride and concentrated under the reduced pressure. By wet-refine process in the column chromatography using hexane and ethylacetate after removing the solvent, the compound "1b" of yellow solid was obtained. (yield: 98%)

(3) Compound 1

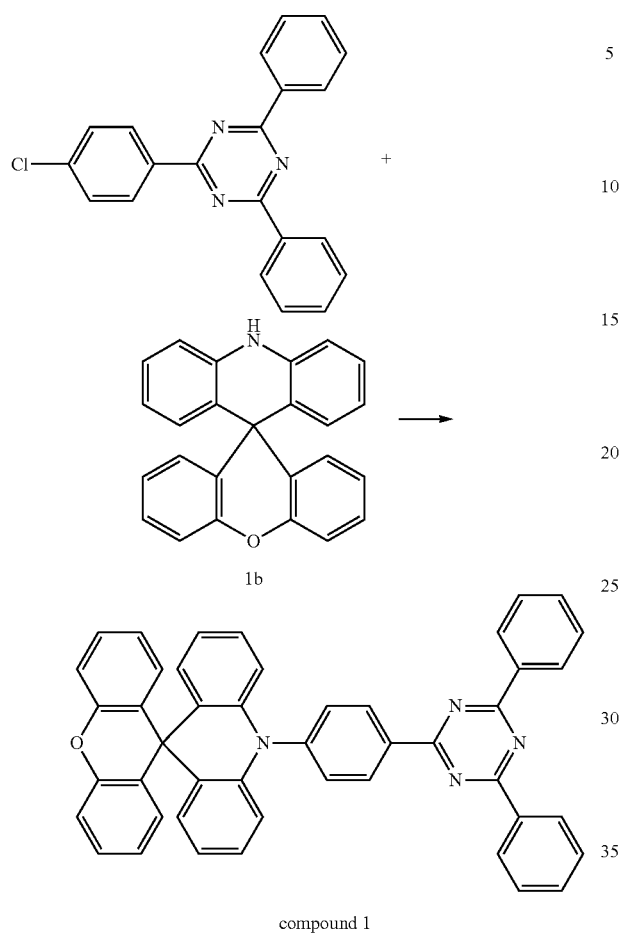

compound 1

In the vacuum-dry flask under the $N_2$ gas purging system, the compound "1b" (70.0 mmol) and 2-(4-chlorophenyl)-4,6-diphenyl-1,3,5-triazine (77.9 mmol) were mixed in the toluene solvent and stirred. After additionally stirring for 30 minutes, t-BuONa (160 mmol), $Pd_2(dba)_3$ (1.00 mmol) and tetra(tert-butyl)porphyrin (TTBuP, 3.00 mmol) were added. The mixture was refluxed and stirred for more than 24 hrs. By wet-refine process in the column chromatography using hexane and methylenechloride after removing the solvent, the compound 1 of light-yellow solid was obtained. (yield: 72%)

Figure 6:
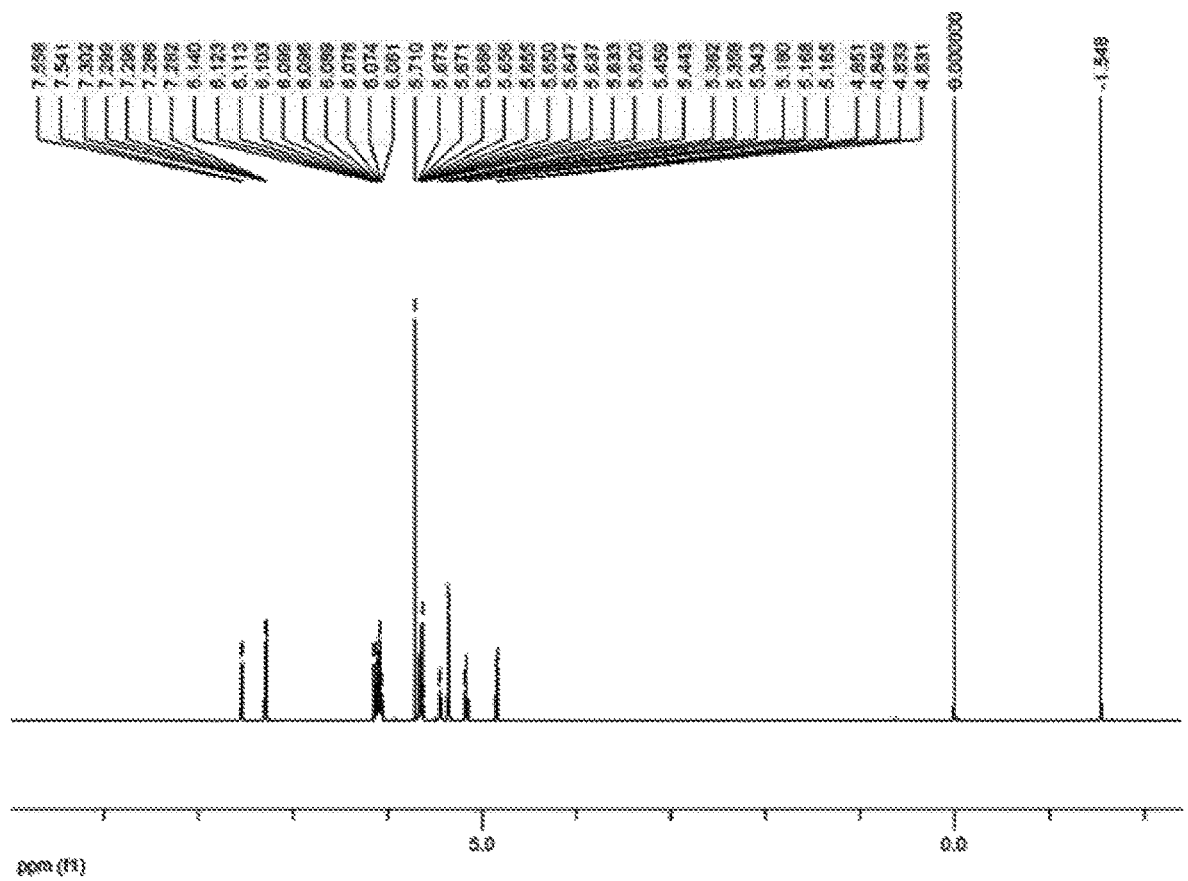
FIG. 6 and FIG. 7 are NMR graphs of organic compounds of the present invention.

The NMR graph of the compound 1 is shown in FIG. 6.

2. Synthesis of Compound 4

(1) Compound "2a"

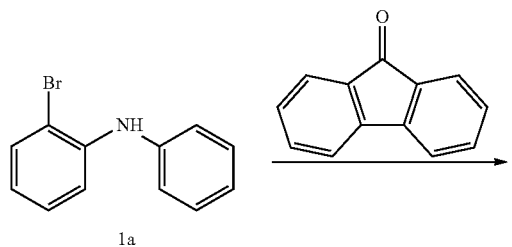

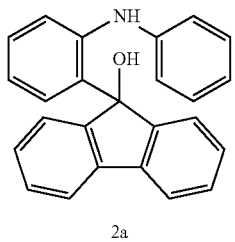

In the vacuum-dry flask under the $N_2$ gas purging system, the compound "1a" (66.1 mmol) and the tetrahydrofuran solvent was stirred for 30 minutes. The mixture was additionally stirred under the temperature of −78° C. for 10 minutes, and butyl-lithium (135 mmol) was slowly dropped. After the mixture was stirred for 60 minutes, fluorenone (72.7 mmol) was added. The mixture was concentrated under the reduced pressure, the organic layer was extracted by $CHCl_3$. The moisture was removed from the extracted organic layer using magnesium sulfate, and the solvent was removed. After the mixture was cooled into the room temperature, the mixture was extracted by methylenechloride and concentrated under the reduced pressure. By wet-refine process in the column chromatography using hexane and ethylacetate after removing the solvent, the compound "2a" of yellow solid was obtained. (yield: 88%)

(2) Compound "2b"

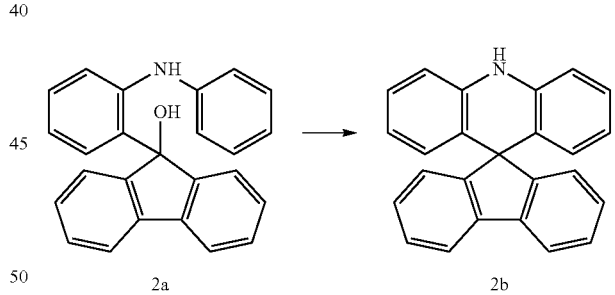

In the vacuum-dry flask under the $N_2$ gas purging system, the compound 2a (66.1 mmol) and the chloroform solvent were stirred. After methansulfonic acid (66.1 mmol) was added, and the mixture was bubbled with Ar gas under the room temperature for about 30 minutes. The mixture was refluxed and stirred for more than 24 hrs. After completion of the reaction, the solvent was removed, and the mixture was extracted using distilled water and ethylacetate. The moisture was removed from the extracted organic layer using magnesium sulfate, and the solvent was removed. By wet-refine process in the column chromatography using hexane and methylenechloride, the compound "2b" of yellow solid was obtained. (yield: 90%)

(3) Compound 4

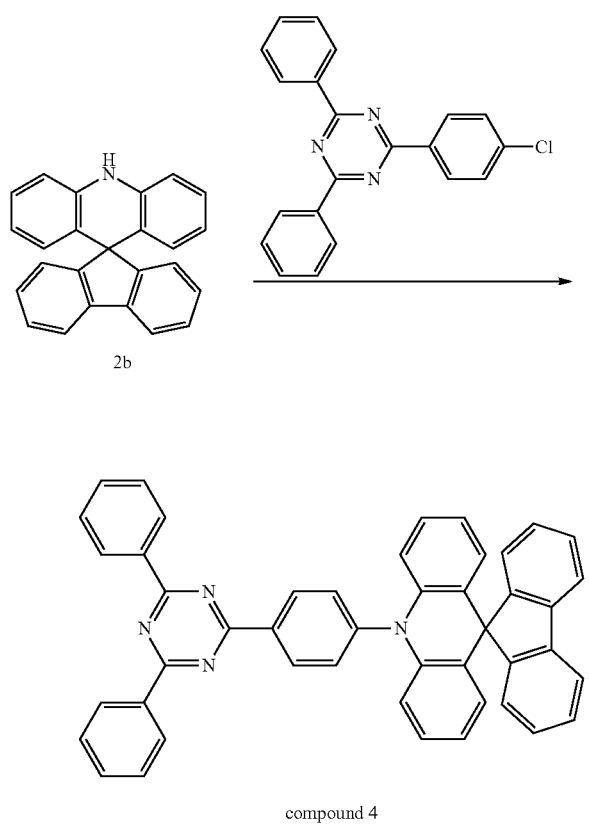

2b compound 4

In the vacuum-dry flask under the N₂ gas purging system, the compound "2b" (70.8 mmol) and 2-(4-chlorophenyl)-4,6-diphenyl-1,3,5-triazine (77.9 mmol) were mixed in the toluene solvent and stirred. After additionally stirring for 30 minutes, t-BuONa (95.7 mmol), Pd₂(dba)₃ (3.50 mmol) and TTBuP (7.00 mmol) were added. The mixture was refluxed and stirred for more than 24 hrs. After completion of the reaction, the mixture was silica-hot filtered by p-xylene and washed by acetone. The resultant was re-crystallized using toluene such that the compound 4 of light-yellow solid was obtained. (yield: 68%)

3. Synthesis of Compound 8

(1) Compound "3a"

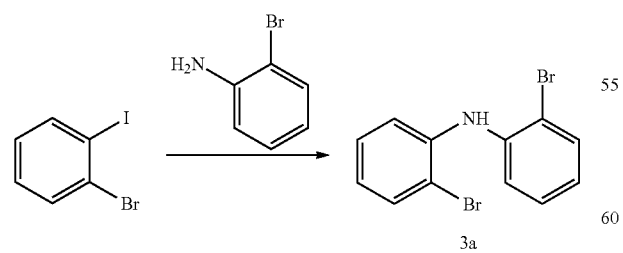

In the N₂ gas purging system, bromoiodobenzene (201 mmol) and the toluene solvent were stirred. 2-bromoaniline (174 mmol) was added, and the mixture was bubbled with Ar gas under the room temperature for about 30 minutes. After sodium t-butoxide (262 mmol) was added, [1,1′-bis(diphenylphosphino)ferrocene]dichloropalldium(II) (Pd(dppf)Cl₂, 17.0 mmol) and Pd₂(dba)₃ (9 mmol) were further added. The mixture was refluxed and stirred for more than 24 hrs. The mixture was silica-filtered by methylenechloride and concentrated under the reduced pressure. By wet-refine process in the column chromatography using hexane and ethylacetate, the compound "3a" of light-yellow liquid was obtained. (yield: 90%)

(2) Compound "3b"

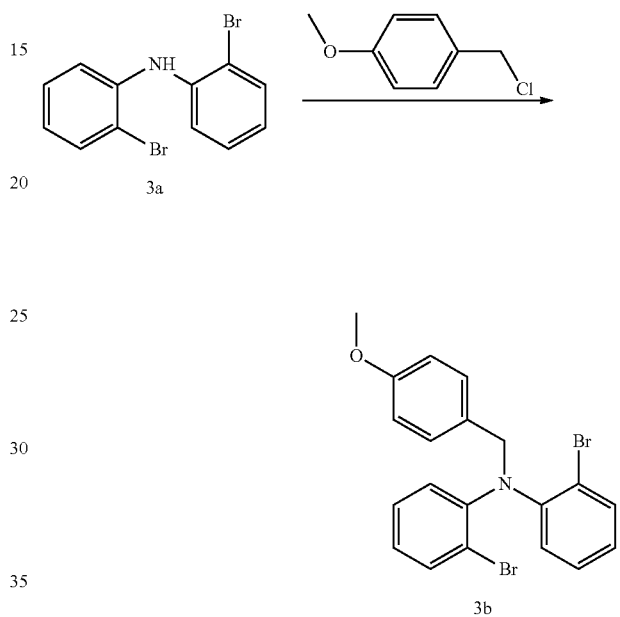

3a

3b

In the vacuum-dry flask under the N₂ gas purging system, the compound "3a" (75.0 mmol) and the dimethylformamide (DMF) solvent were mixed and stirred. After the mixture was further stirred under the temperature of 0° C. for 10 minutes, NaH (225 mmol) was slowly dropped. After further stirring for 60 minutes, 4-methoxybenzyl chloride (75.0 mmol) was added and stirred for more than 4 hrs. After excess water was added, the mixture was filtered. By washing with hexane, the compound "3b" of light-yellow solid was obtained. (yield: 81%)

(3) Compound "3c"

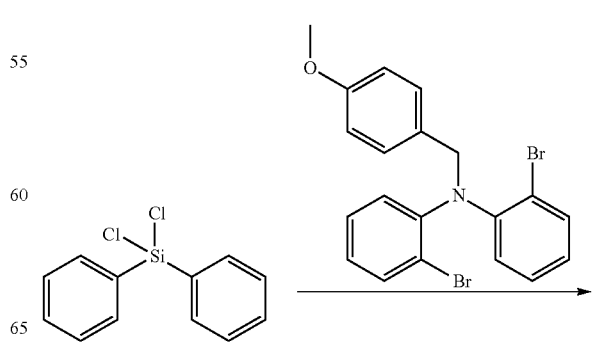

-continued

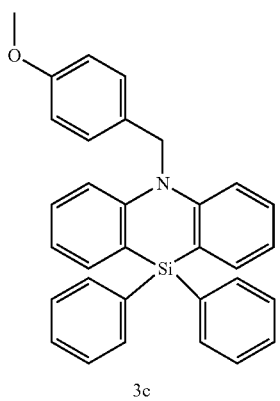
3c

In the vacuum-dry flask under the $N_2$ gas purging system, the compound "3b" (60.0 mmol) and the tetrahydrofuran solvent was stirred for 30 minutes. The mixture was additionally stirred under the temperature of −78° C. for 10 minutes, and butyl-lithium (120 mmol) was slowly dropped. After the mixture was stirred for 60 minutes, dichlorodiphenylsilane (70.0 mmol) was added and stirred for more than 3 hrs. After excess water was added, the mixture was filtered. By washing with ether, the compound "3c" of light-yellow solid was obtained. (yield: 71%)

(4) Compound "3d"

3c → 3d

In the vacuum-dry flask under the $N_2$ gas purging system, the compound "3c" (40.0 mmol), 2,3-dichloro5,6-dicyano-1,4-benzoquinone (49 mmol) and the toluene solvent were stirred under the temperature of 80° C. for more than 14 hrs. The mixture was silica-filtered with ethyleneacetate and concentrated under the reduced pressure. By wet-refine process in the column chromatography using hexane and ethylacetate, the compound "3d" of light-yellow solid was obtained. (yield: 90%)

(5) Compound 8

3d + [triazine reagent] → compound 8

In the vacuum-dry flask under the $N_2$ gas purging system, the compound "3d" (5.70 mmol) and 2-(4-chlorophenyl)-4,6-diphenyl-1,3,5-triazine (6.90 mmol) were mixed in the toluene solvent and stirred. After additionally stirring for 30 minutes, t-BuONa (12.6 mmol), $Pd_2(dba)_3$ (0.10 mmol) and TTBuP (0.20 mmol) were added. The mixture was refluxed and stirred for more than 24 hrs. After completion of the reaction, the mixture was silica-hot filtered by methylenechloride. The resultant was re-crystallized using toluene such that the compound 8 of light-yellow solid was obtained. (yield: 58%)

Figure 7:
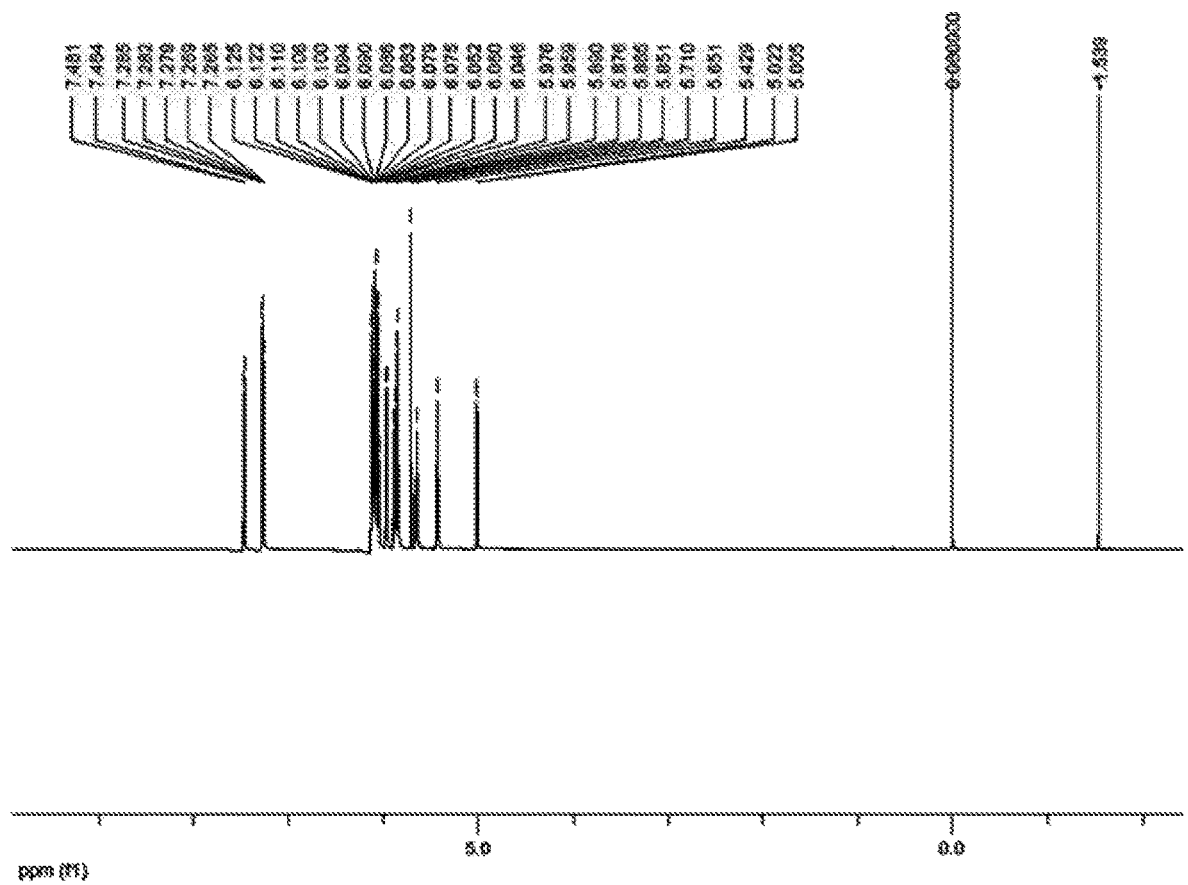

The NMR graph of the compound 8 is shown in FIG. 7.

PL Intensity

Figure 8:
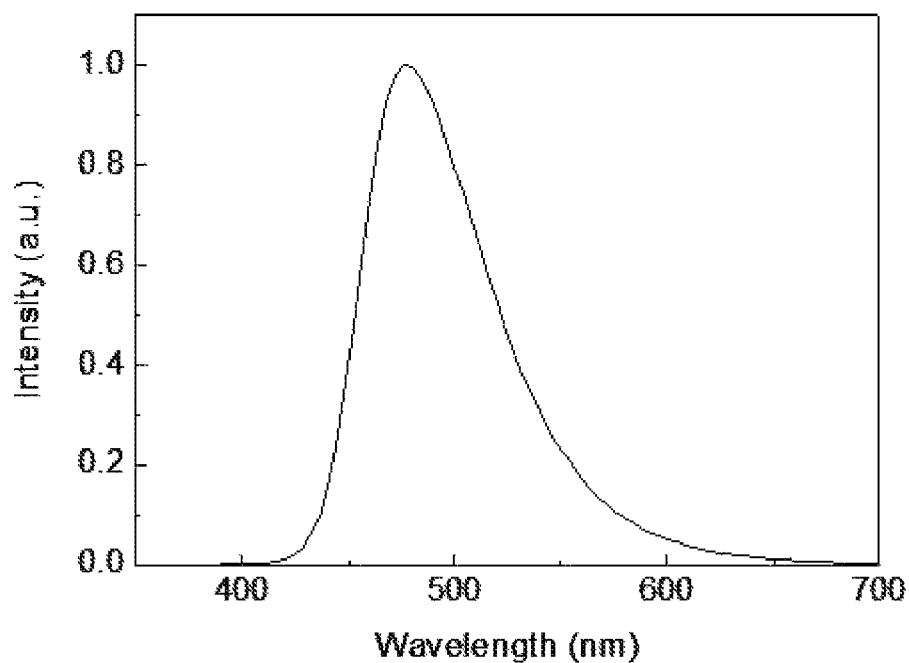
FIG. 8, FIG. 9 and FIG. 10 are graphs showing a photoluminescence (PL) intensity of organic compounds of the present invention.
Figure 9:
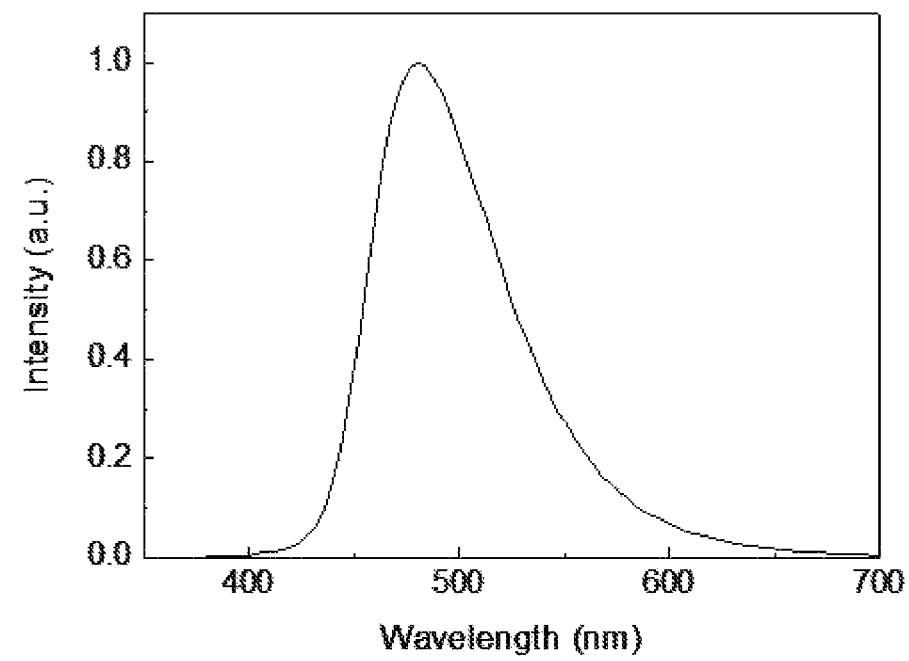
Figure 10:
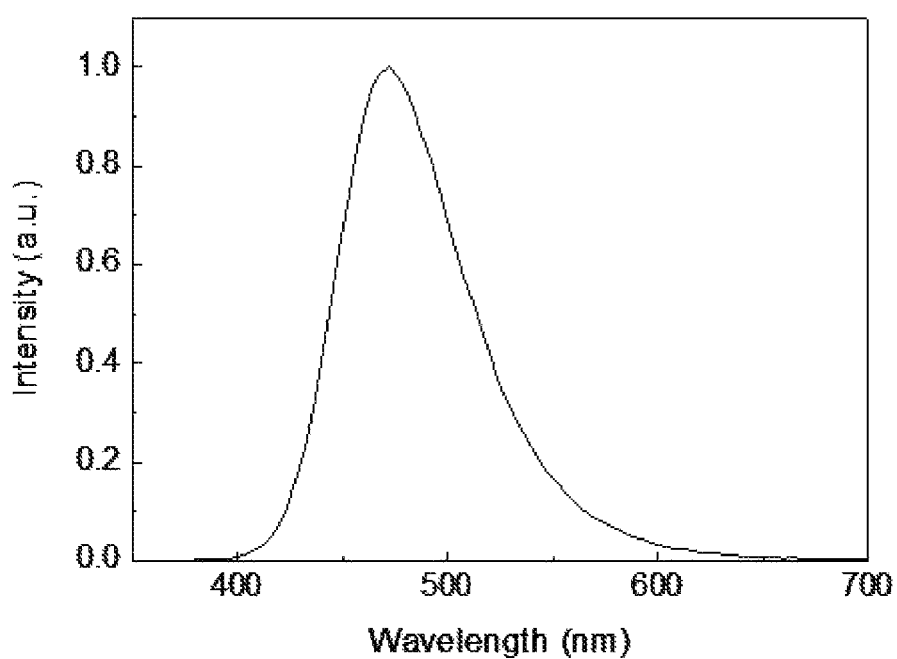
Figure 11:
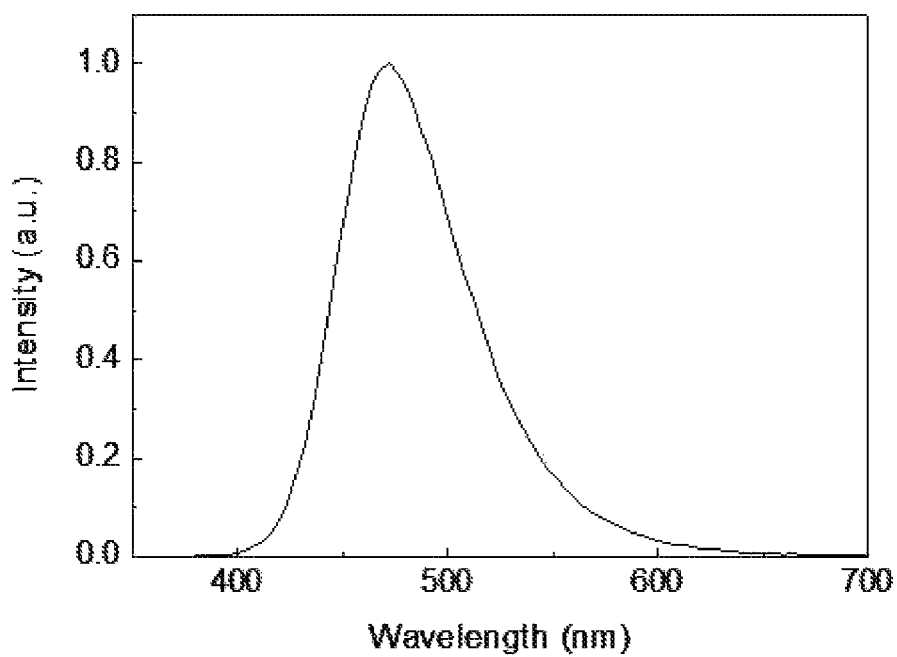

The photoluminescence (PL) intensity of the compounds 1, 4 and 8 is measured. The PL intensity is measured under the room temperature with the solvent of dichloromethane. The PL intensity of the compounds 1, 4 and 8 are shown in FIGS. 8 to 10, and a maximum emission peak (λ max) and a full width at half maximum (FWHM) are listed in Table 1. As shown in FIGS. 8 to 10, the compounds 1, 4 and 8 emit the blue light.

TABLE 1

|  | Λ max [nm] | FWHM [nm] |
|---|---|---|
| Compound 1 | 476 | 72 |
| Compound 4 | 476 | 69 |
| Compound 8 | 476 | 70 |

Organic Light Emitting Diode

1. Example 1 (Ex1)

An ITO substrate, which includes a reflection layer, of 40*40 mm with a thickness of 0.5 mm is ultrasonic-cleaned with isopropyl alcohol, acetone and DI water for 5 minutes and dried in 100° C. oven. Then, the $O_2$ plasma treatment is performed onto the ITO substrate for 2 minutes, and the ITO substrate is transferred into a deposition chamber. Under the vacuum condition of about $10^{-7}$ torr, following layers are deposited.

(1) HIL (HAT-CN, 7 nm), (2) HTL (NPB, 55 nm), (3) EBL (mCBP, 10 nm), (4) EML (mCP—CN (host) and the compound 1 (dopant, 30 wt % doping), 25 nm), (5) HBL (B3PYMPM, 10 nm), (6) ETL (TPBi, 20 nm), (7) EIL (LiF), and (8) cathode (Al).

After a capping layer is further formed, the organic light emitting diode is encapsulized by glass. The deposited structure is loaded in the drying box and encapsuled by an UV-cured expoxy and a getter.

2. Example 2 (Ex2)

Instead of the compound 1, the compound 4 is used.

3. Example 3 (Ex3)

Instead of the compound 1, the compound 8 is used.

4. Comparative Example (Ref)

Instead of the compound 1, a compound (9-(4-(4,6-diphenyl-1,3,5-triazin-2-yl)phenyl)-3,6-bis(3,6-diphenyl-9H-carbazol-9-yl)-9H-carbazole (2Ph-3Cz-TRZ)) of Formula 5 is used.

[Formula 5]

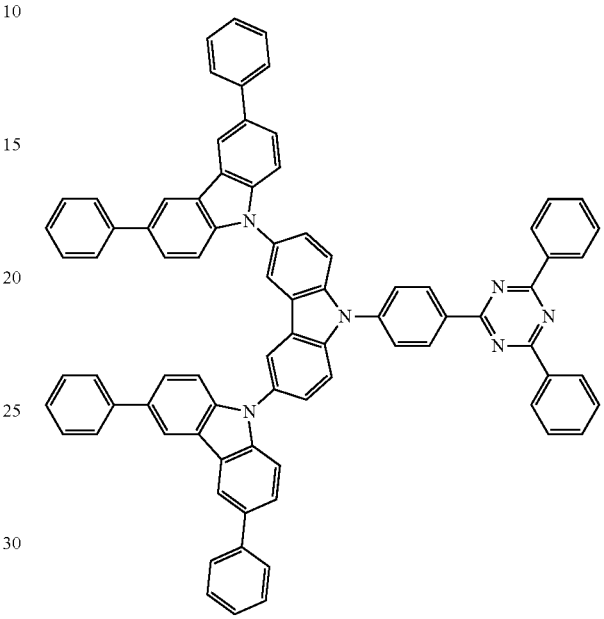

The properties of the organic light emitting diodes of "Ex1" to "Ex3" and "Ref", each of which has an emission area of 9 mm², are measured using the current supply "KEITHLEY" and the photometer "PR 650" under the room temperature. The driving voltage (V), the current efficiency (cd/A), the power efficiency (lm/W), the external quantum efficiency (EQE), the luminance (cd/m²) and the color coordinate index of the organic light emitting diodes of are measured and listed in Table 2.

TABLE 2

|  | V | (cd/A) | lm/W | EQE (%) | cd/m² | CIE(X) | CIE(Y) |
|---|---|---|---|---|---|---|---|
| Ref | 4.66 | 14.20 | 9.58 | 6.29 | 1420 | 0.20 | 0.42 |
| Ex1 | 3.67 | 23.03 | 19.72 | 12.88 | 2303 | 0.16 | 0.30 |
| Ex2 | 3.72 | 18.24 | 15.39 | 12.08 | 1824 | 0.15 | 0.22 |
| Ex3 | 3.47 | 12.45 | 11.27 | 8.00 | 1245 | 0.14 | 0.25 |

As shown in Table 2, in comparison to the organic light emitting diode of "Comparative Example" (Ref), the organic light emitting diode using the organic compound as a dopant has advantages in the driving voltage, the current efficiency, the power efficiency, the EQE and the luminance. In addition, the organic light emitting diode using the organic compound as the dopant provides the deep blue light. Namely, the organic compound of the present invention is used as the dopant in the EML such that the emitting efficiency and the color purity of the organic light emitting diode are improved. The organic light emitting diode may be used for the organic light emitting display device and/or the lightening device.

It will be apparent to those skilled in the art that various modifications and variations can be made in the embodiment of the invention without departing from the spirit or scope of the invention. Thus, it is intended that the embodiment of the invention cover the modifications and variations of this invention provided they come within the scope of the appended claims and their equivalents.

What is claimed is:

1. An organic light emitting diode, comprising:
   a first electrode;
   a second electrode facing the first electrode; and
   an organic emitting layer between the first electrode and the second electrode, the organic emitting layer including the organic compound of Formula 1:

[Formula 1]

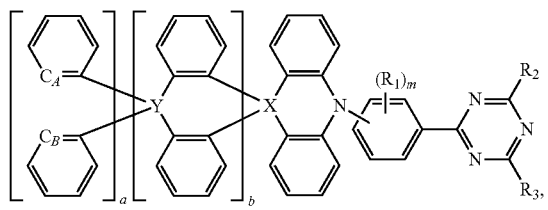

wherein each of $R_1$ to $R_3$ is independently selected from the group consisting of hydrogen, deuterium, tritium, substituted $C_1$ to $C_{20}$ alkyl group, non-substituted $C_1$ to $C_{20}$ alkyl group, substituted $C_1$ to $C_{20}$ alkoxy group, non-substituted $C_1$ to $C_{20}$ alkoxy group, substituted $C_3$ to $C_{30}$ cycloalkyl group, non-substituted $C_3$ to $C_{30}$ cycloalkyl group, substituted $C_3$ to $C_{30}$ hetero-cycloalkyl group, non-substituted $C_3$ to $C_{30}$ hetero-cycloalkyl group, substituted $C_5$ to $C_{30}$ aryl group, non-substituted $C_5$ to $C_{30}$ aryl group, substituted $C_4$ to $C_{30}$ heteroaryl group, and non-substituted $C_4$ to $C_{30}$ heteroaryl group,
   wherein each of "a" and "b" is an integer of 0 to 2,
   wherein at least one of "a" and "b" is a positive integer, and "m" is an integer of 1 to 4,
   wherein each of X and Y is independently carbon or silicon,
   wherein each of $C_A$ and $C_B$ is carbon,
   wherein each of $C_A$ and $C_B$ has a substituent selected from the group consisting of hydrogen, deuterium, tritium, substituted $C_1$ to $C_{20}$ alkyl group, non-substituted $C_1$ to $C_{20}$ alkyl group, substituted $C_1$ to $C_{20}$ alkoxy group, and non-substituted $C_1$ to $C_{20}$ alkoxy group,
   wherein each of the substituted $C_1$ to $C_{20}$ alky group, the non-substituted $C_1$ to $C_{20}$ alkyl group, the substituted $C_1$ to $C_{20}$ alkoxy group, and the non-substituted $C_1$ to $C_{20}$ alkoxy group is directly bonded or indirectly bonded via oxygen (O), sulfur (S) or selenium (Se),
   wherein the organic compound is suitable for use as a dopant, and the organic emitting layer further includes a host,
   wherein the organic compound exhibits a difference between a highest occupied molecular orbital (HOMO) of the host and a HOMO of the dopant that is less than or equal to 0.5 eV, or
   wherein the organic compound exhibits a difference between a lowest unoccupied molecular orbital (LUMO) of the host and a LUMO of the dopant that is less than or equal to 0.5 eV.

2. The organic light emitting diode according to claim 1, wherein a difference between a single energy level of the organic compound and a triplet energy level of the organic compound is less than 0.3 eV.

3. An organic light emitting display device, comprising:
   a substrate; and
   the organic light emitting diode of claim 1 disposed on the substrate.

4. The organic light emitting display device according to claim 3, further comprising an encapsulation film on the organic light emitting diode.

5. The organic light emitting display device according to claim 3, wherein a difference between a single energy level of the organic compound and a triplet energy level of the organic compound is less than 0.3 eV.

6. The organic light emitting diode according to claim 1, wherein the organic compound is represented by Formula 2 or Formula 3:

[Formula 2]

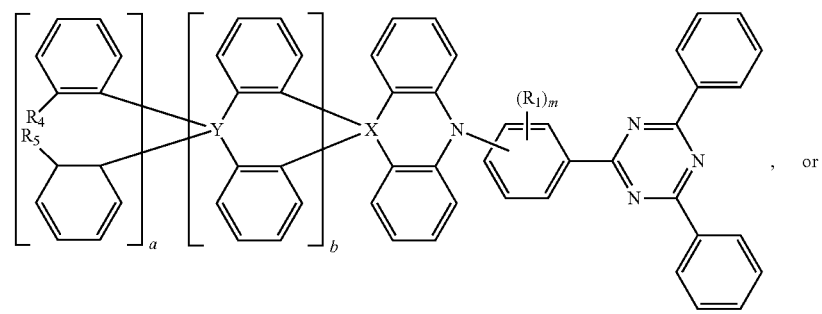

, or

-continued

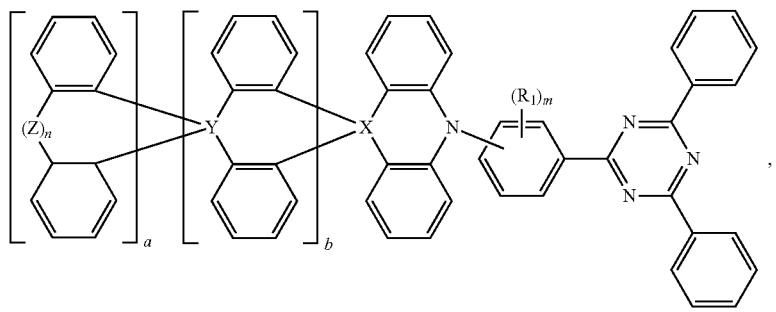

wherein R₁ is selected from the group consisting of hydrogen, deuterium, tritium, substituted $C_1$ to $C_{20}$ alkyl group, non-substituted $C_1$ to $C_{20}$ alkyl group, substituted $C_1$ to $C_{20}$ alkoxy group, non-substituted $C_1$ to $C_{20}$ alkoxy group, substituted $C_3$ to $C_{30}$ cycloalkyl group, non-substituted $C_3$ to $C_{30}$ cycloalkyl group, substituted $C_3$ to $C_{30}$ hetero-cycloalkyl group, non-substituted $C_3$ to $C_{30}$ hetero-cycloalkyl group, substituted $C_5$ to $C_{30}$ aryl group, non-substituted $C_5$ to $C_{30}$ aryl group, substituted $C_4$ to $C_{30}$ heteroaryl group, and non-substituted $C_4$ to $C_{30}$ heteroaryl group, wherein each of "a" and "b" is an integer of 0 to 2, wherein at least one of "a" and "b" is a positive integer, and "m" is an integer of 1 to 4, wherein each of X and Y is independently carbon or silicon, wherein each of $R_4$ and $R_5$ in Formula 2 is independently selected from the group consisting of hydrogen, deuterium, tritium and C1 to C20 alkyl group, and wherein Z in Formula 3 is oxygen, sulfur or selenium, and n is 0 or 1.

7. The organic light emitting diode according to claim 1, wherein the organic compound is selected from:

compound 1

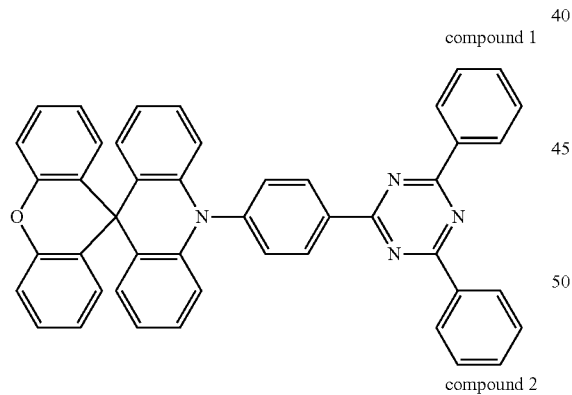

compound 2

[Formula 3]

compound 3

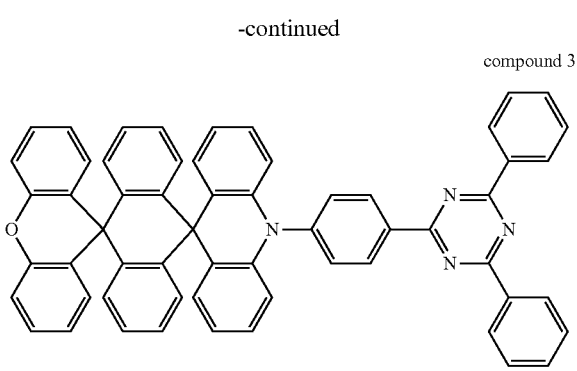

compound 4

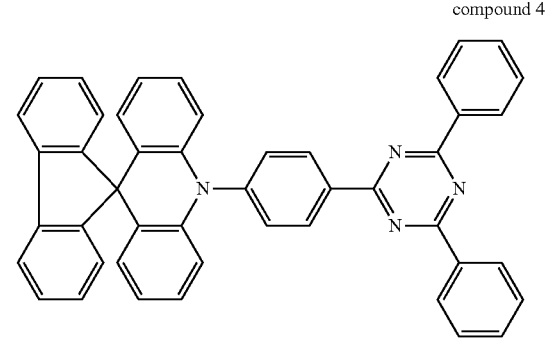

compound 5

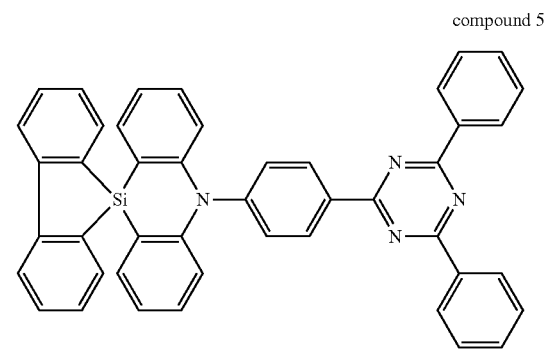

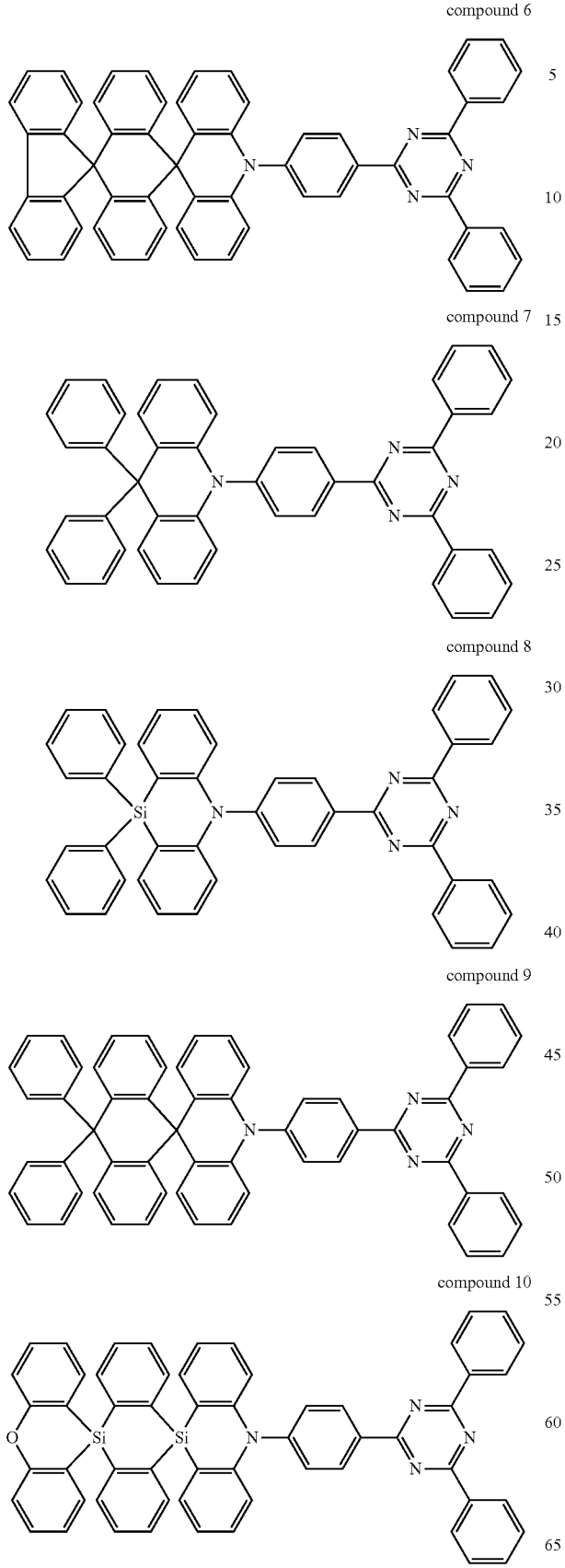

compound 6 compound 7 compound 8 compound 9 compound 10

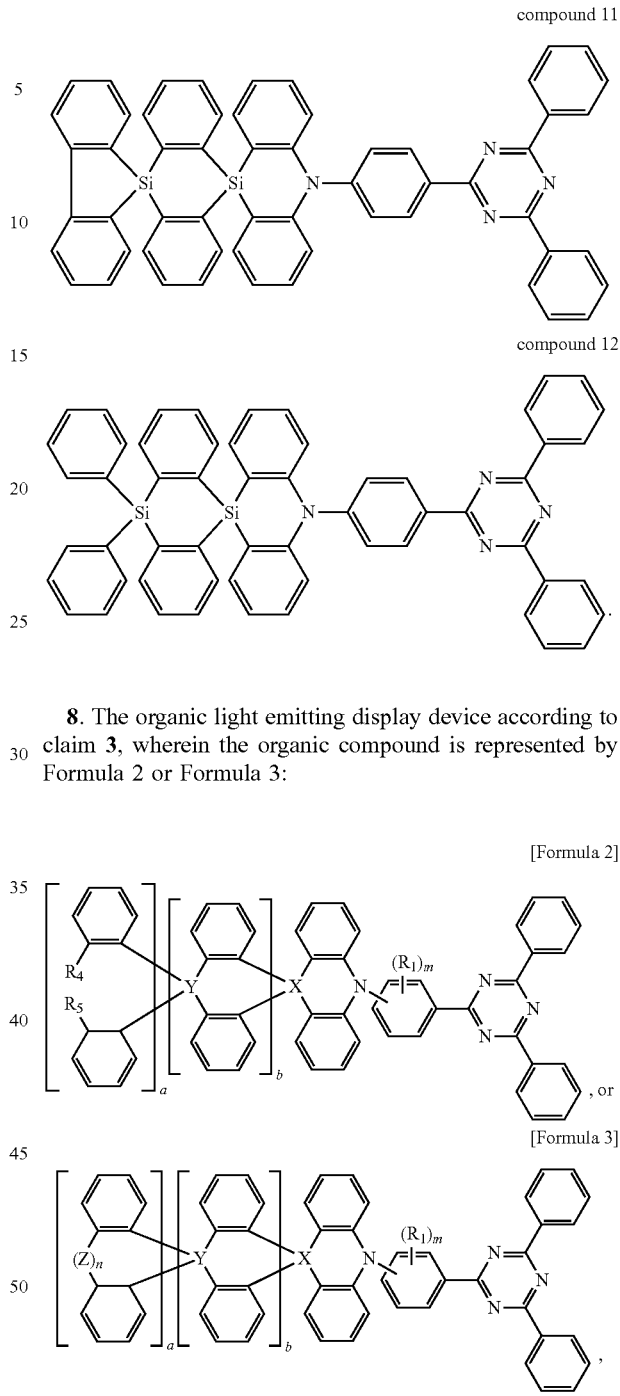

compound 11 compound 12

8. The organic light emitting display device according to claim 3, wherein the organic compound is represented by Formula 2 or Formula 3:

[Formula 2]

, or

[Formula 3]

wherein $R_1$ is selected from the group consisting of hydrogen, deuterium, tritium, substituted $C_1$ to $C_{20}$ alkyl group, non-substituted $C_1$ to $C_{20}$ alkyl group, substituted $C_1$ to $C_{20}$ alkoxy group, non-substituted $C_1$ to $C_{20}$ alkoxy group, substituted $C_3$ to $C_{30}$ cycloalkyl group, non-substituted $C_3$ to $C_{30}$ cycloalkyl group, substituted $C_3$ to $C_{30}$ hetero-cycloalkyl group, non-substituted $C_3$ to $C_{30}$ hetero-cycloalkyl group, substituted $C_5$ to $C_{30}$ aryl group, non-substituted $C_5$ to $C_{30}$ aryl group, substituted $C_4$ to $C_{30}$ heteroaryl group, and non-substituted $C_4$ to $C_{30}$ heteroaryl group, wherein each of "a" and "b" is an integer of 0 to 2,
wherein at least one of "a" and "b" is a positive integer, and "m" is an integer of 1 to 4,
wherein each of X and Y is independently carbon or silicon,
wherein each of $R_4$ and $R_5$ in Formula 2 is independently selected from the group consisting of hydrogen, deuterium, tritium and C1 to C20 alkyl group, and
wherein Z in Formula 3 is oxygen, sulfur or selenium, and n is 0 or 1.

9. The organic light emitting display device according to claim 3, wherein the organic compound is selected from:

compound 1

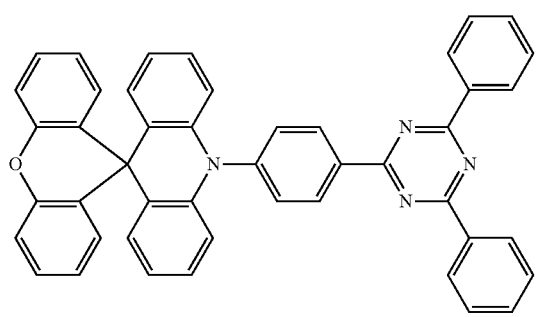

compound 2

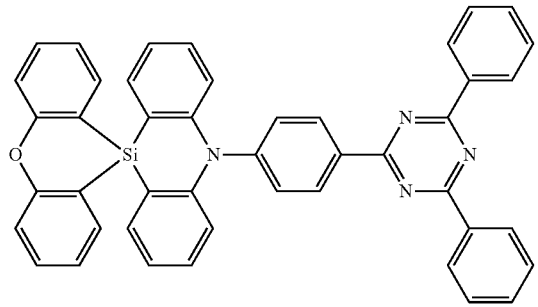

compound 3

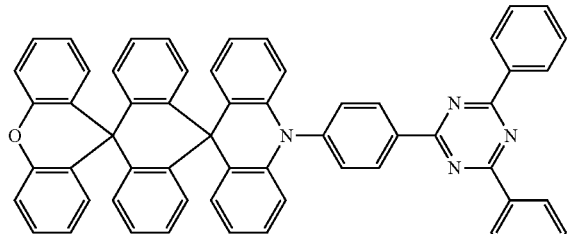

compound 4

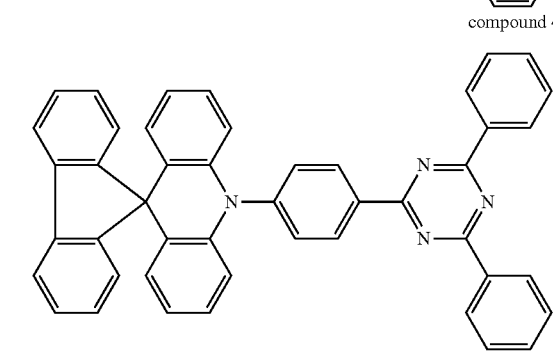

compound 5

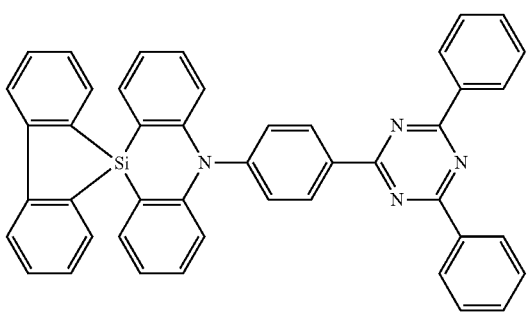

compound 6

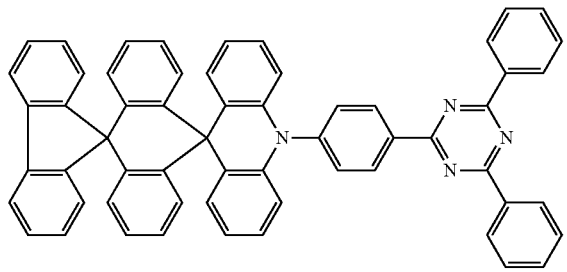

compound 7

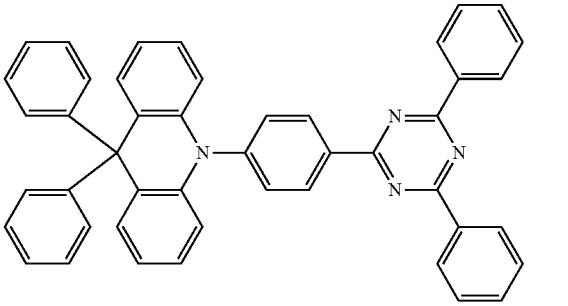

compound 8

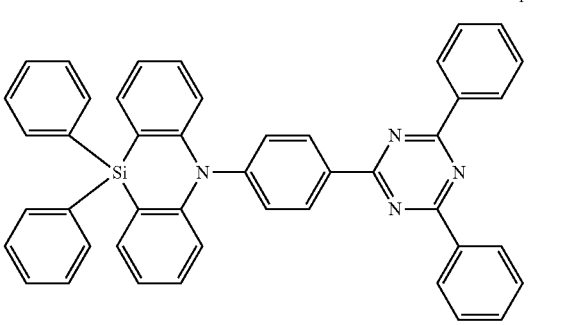

-continued
compound 9
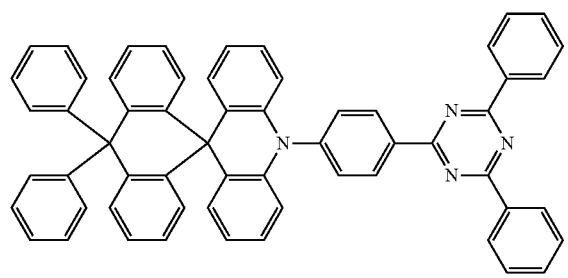
compound 10
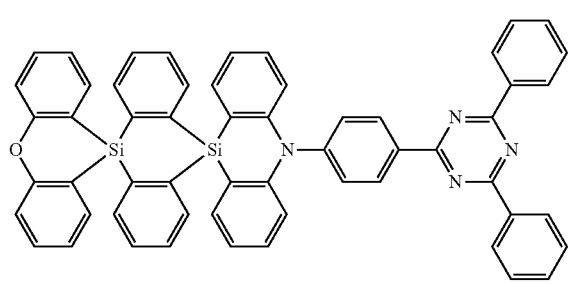
compound 11
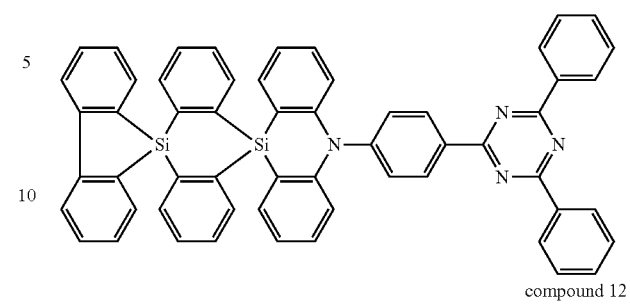
compound 12
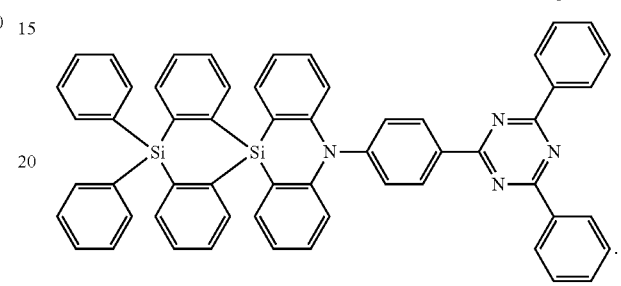
* * * * *